United States Patent [19]

Schaap

[11] Patent Number: 5,004,565
[45] Date of Patent: Apr. 2, 1991

[54] METHOD AND COMPOSITIONS PROVIDING ENHANCED CHEMILUMINESCENCE FROM 1,2-DIOXETANES

[75] Inventor: Arthur P. Schaap, Detroit, Mich.

[73] Assignee: The Board of Governors of Wayne State University, Detroit, Mich.

[21] Appl. No.: 224,681

[22] Filed: Jul. 27, 1988

Related U.S. Application Data

[63] Continuation-in-part of Ser. No. 887,139, Jul. 17, 1986.

[51] Int. Cl.$^5$ .......................... C08F 8/00; C09K 3/00; B01J 13/00
[52] U.S. Cl. ................................... 252/700; 435/147; 435/148; 436/829; 436/905; 424/450; 252/311; 428/402
[58] Field of Search .................. 549/510, 511, 332; 252/700, 301.16, 301.34, 301.35, 311; 435/147, 148; 436/829, 905; 424/450; 428/402

[56] References Cited

U.S. PATENT DOCUMENTS 4,315,998  2/1982  Neckers et al. ...................... 525/332

FOREIGN PATENT DOCUMENTS

88/00695  1/1988  PCT Int'l Appl. .

OTHER PUBLICATIONS

Zimmerman, "Photochemcial Rearrangement Without Light . . . ", J. Am. Chem. Soc. 97(12), 3527-8, 1975.
Wong & Wilson, "Products of . . . Trihydroxychalcone", Phytochemistry 1976, vol. 15, pp. 1325-1332.
Wilson & Wong, "Trihydroxychalcone", Phytochemistry 1976, vol. 15, pp. 1333-1341.
Wong, "Photooxygenation of 2',4,4'-Trihydroxychalcone . . . ", Phytochemistry, vol. 26, No. 5, pp. 1544-1545, 1987.
Schaap et al., "Chemical and Enzymatic Triggering . . . ", Tetrahedron Lett. 28(9) 935-8, 1987.
Schaap et al., "Chemical and Enzymatic Triggering . . . ", Tetrahedron Lett. 28(11) 1155-8, 1987.
Schaap et al., "Mechanisms of Photooxygenation . . . ", J. Am. Chem. Soc. 102 (1), 389-91, 1980.
Jefford et al., "Oxygenation of 3-Aryl-2-Hydroxy Acrylic . . . ", J. Am. Chem. Soc., 100(20), 6432-6, 1978.
Richardson et al., "Substituent Effects Upon Efficiency . . . ", J. Org. Chem., 52(14), 3143-50, 1987.
Wong, "Products from Enzymatic Oxidation . . . ", Tetrahedron Lett., 25(25), 2631-4, 1984.
Richardson et al., "Electronic Effects . . . ", J. Am. Chem. Soc. 104(15), 4173-9, 1982.
Richardson et al., "Substituent Effects . . . ", J. Org. Chem. 50(11), 1803-10, 1985.
Zimmerman et al., "Molecular Rearrangements . . . ", J. Am. Chem. Soc. 98 (18), 5574-81, 1976.
The Chemistry of Synthetic Dyes, vol. VII, K. Venkataraman, 1974, 304-305.
Merck Index, 10th Ed., p. 8138.
McCapra, F., Chem. Commun., 155 (1968).
Shimomura et al., Photochem. Photobiol., 30, 89 (1979).
K. R. Kopecky et al., Can. J. Chem., 47, 709 (1969).
P. D. Bartlett et al., J. Amer. Chem. Soc., 92, 3223 (1970).
S. Mazur et al., J. Amer. Chem. Soc., 92, 3225 (1970).
A. P. Schaap et al., J. Amer. Chem. Soc., 99, 1270 (1977).
K. A. Zaklika et al., J. Amer. Chem. Soc., 100, 318 (1978).

(List continued on next page.)

Primary Examiner—Mary C. Lee
Assistant Examiner—Catherine Scalzo
Attorney, Agent, or Firm—Ian C. McLeod

[57] ABSTRACT

A method and compositions including a 1,2-dioxetane and a fluorescent compound is described. In particular, enzymatic triggering of a triggerable 1,2-dioxetane admixed with a surfactant and the fluorescent compound attached to a hydrocarbon to provide a co-surfactant in a micelle or other structure providing close association of these molecules is described. The method and compositions are useful in immunoassays and in DNA probes used for various purposes.

35 Claims, 9 Drawing Sheets

OTHER PUBLICATIONS

K. A. Zaklika et al., J. Amer. Chem. Soc. 100, 4916 (1978).
K. A. Zaklika et al., Photochem. Photobiol., 30, 35 (1979).
A. P. Schaap et al., Organic Photochemical Synthesis, II, 49 (1976).
A. P. Schaap et al., J. Amer. Chem. Soc., 97, 3741 (1975).
A. P. Schaap et al., J. Amer. Chem. Soc., 101, 4016 (1979).
J. H. Wieringa et al., Tetrahedron Lett., 169 (1972).
N. J. Turro et al., J. Amer. Chem. Soc., 97, 7110 (1975).
A. P. Schaap, J. Amer. Chem. Soc., 97, 3741 (1975).
W. Adam et al., Z. Naturforsch., 39b, 679 (1984).
H. Wynberg et al., Bioluminescence and Chemiluminescence, M. A. Deluca & W. D. McElroy (Eds.) Academic Press, N.Y., p. 687 (1981).
J. C. Hummelen et al., Methods in Enzymology, 133B, 531 (1986).
McCapra et al., J. Chem. Soc., Chem. Commun., 944 (1977).
W. Adam et al., Chem. Ber., 116, 839 (1983).
G. Geller et al., Tetrahedron Lett., 673 (1983).
P. Lechtken, Chem. Ber., 109, 2862 (1976).
P. D. Bartlett et al., J. Amer. Chem. Soc., 96, 627 (1974).
A. P. Schaap et al., J. Amer. Chem. Soc., 104, 3504 (1982).
A. P. Schaap et al., Tetrahedron Lett., 2943 (1982).
R. S. handley et al., Tetrahedron Lett., 3183 (1985).
T. Wilson, Int. Rev. Sci.: Chem., Ser. Two, 9, 265 (1976).
T. Wilson et al., J. Amer. Chem. Soc., 95, 4765 (1973).
P. D. Bartlett et al., J. Amer. Chem. Soc., 96, 5557 (1974).
T. Wilson et al., J. Amer. Chem. Soc., 93, 4126 (1971).
W. Adam in Chemical & Biological Generation of Excited States, W. Adam & Cilento, Eds. Ch. 4, Academic Press, N.Y. (1982).
E. H. Cordes et al., Acc. Chem. Res., 2,329 (1969).
A. P. Schaap, Final Technical Report to the Office of Naval Research, 1987, p. 16.
T. Goto et al., Tetrahedron Lett., 4299 (1969).
F. McCapra, Acc. Chem. Res., 9, 201 (1976).
C. M. Paleos et al., Bioluminescence and Chemiluminescence, Acad. Press, N.Y., 1981, p. 729.
K. D. Gundermann, IBID., p. 17.
S. Shinkai et al., Chem. Lett., 1523 (1981).
L. J. Kricka et al., Arch. Biochem. Biophys., 217, 674 (1983).
G. H. Thorpe et al., Clin Chem., 31, 1335 (1985).
G. H. Thorpe et al., Methods in Enzymology, 133, 331 (1986).
L. J. Kricka et al., Pure & Appl. Chem., 59, 651 (1987).
Y. Kubota et al., Bull. Chem. Soc., Jpn., 46, 100 (1973).
N. E. Shore et al., J. Amer. Chem. Soc., 96, 306 (1974).
G. W. Pohl, Z. Naturforsch., 31c, 575 (1976).
H. R. Schroeder et al., Anal. Chem. 50, 1114 (1978).
H. Arakawa et al., Anal. Biochem, 79, 248 (1979).
H. Arakawa et al., Clin. Chem., 31, 430 (1985).
L. J. Kricka and T. J. N. Carter, Clinical and Biochem. Luminescence, L. Kricka & T. Carter (Eds.) Marcel Dekker, Inc., N.Y., 1982, Ch. 8.
L. J. Kricka, Ligand-Binder Assays, Marcel Dekker, Inc. N.Y. 1985, Ch. 7.
F. McCapra et al., in Bioluminescence & Chemiluminescence: Instru & Appl., vol. I, K. Van Dyke (Ed) CRC Press, Inc., New York, 1985, Ch. 2.
G. J. R. Barnard et al., Ibid., Ch. 7 (1985).
L. J. Kricka et al., Methods in Enzymology, 133, 404 (1986).
M. Leong et al., Cytochem., 34, 1645 (1986).
R. A. Bunce et al., Analyst, 110, 657 (1985).
J. Matthews et al., Anal. Biochem., 151, 205 (1985).
G. Thorpe et al., Clin. Chem., 30, 806 (1984).
Catalysis in Micellar and Macromolecular Systems, Published by Aca Press, (1975), Chapt. 1, pp. 1–18.
A. P. Schaap et al., Tetrahedron Lett., 1155, 935, 1159 (1987).
J. E. McMurry et al., J. Amer. Chem. Soc., 105, 1660 (1983).
J. Lee and H. H. Seliger, Photochem. Photobiol., 15, 227 (1972).
P. R. Michael and L. R. Faulkner, Anal. Chem., 48, 1188 (1976).
L. A. Donoso et al., Investigative Ophthalmology & Visual Science, 26, 561 (1985).

METHOD AND COMPOSITIONS PROVIDING ENHANCED CHEMILUMINESCENCE FROM 1,2-DIOXETANES

CROSS-REFERENCE TO RELATED APPLICATION

This application is a continuation-in-part of U.S. Pat. application Ser. No. 887,139, filed Jul. 17, 1986.

BACKGROUND OF THE INVENTION (1) State of the Invention

The present invention relates to compositions containing a fluorescent compound and a stable 1,2-dioxetane which can be triggered by chemical reagents including enzymes and generate enhanced chemiluminescence. In particular the present invention relates to a method for significantly enhancing the chemiluminescence which involves intermolecular energy transfer to a fluorescent compound in an organized assembly, such as a micelle, which maintains a close spacing between the dioxetane and the fluorescent compound.

(2) Prior Art

1. Mechanisms of Luminescence. Exothermic chemical reactions release energy during the course of the reaction. In virtually all cases, this energy is in the form of vibrational excitation or heat. However, a few chemical processes generate light or chemiluminescence instead of heat. The mechanism for light production involves thermal or catalyzed decomposition of a high energy material (frequently an organic peroxide such as a 1,2-dioxetane) to produce the reaction product in a triplet or singlet electronic excited states. Fluorescence of the singlet species results in what has been termed direct chemiluminescence. The chemiluminescence quantum yield is the product of the quantum yields for singlet chemiexcitation and fluorescence. These quantities are often expressed as efficiencies where efficient (%) = $\Phi \times 100$. Energy transfer from the triplet or singlet product to a fluorescent acceptor can be utilized to give indirect chemiluminescence. The quantum yield for indirect chemiluminescence is the product of the quantum yields for singlet or triplet chemiexcitation, energy transfer, and fluorescence of the energy acceptor.

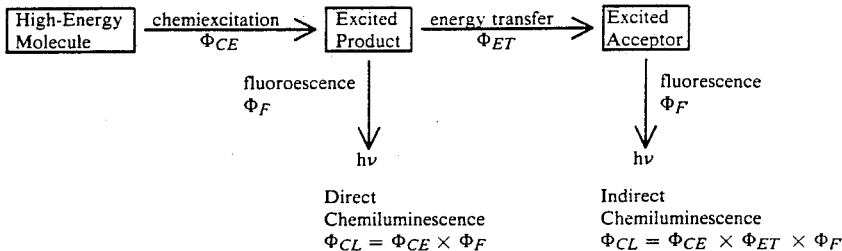

2. Dioxetane Intermediates in Bioluminescence. In 1968 McCapra proposed that 1,2-dioxetanes might be the key high-energy intermediates in various bioluminescent reactions including the firefly system. (F. McCapra *Chem. Commun.*, 155 (1968)). Although this species is apparently quite unstable and has not been isolated or observed spectroscopically, unambiguous evidence for its intermediacy in the reaction has been provided by oxygen-18 labeling experiments (O. Shimomura and F. H. Johnson, *Photochem. Photobiol.*, 30, 89 (1979)).

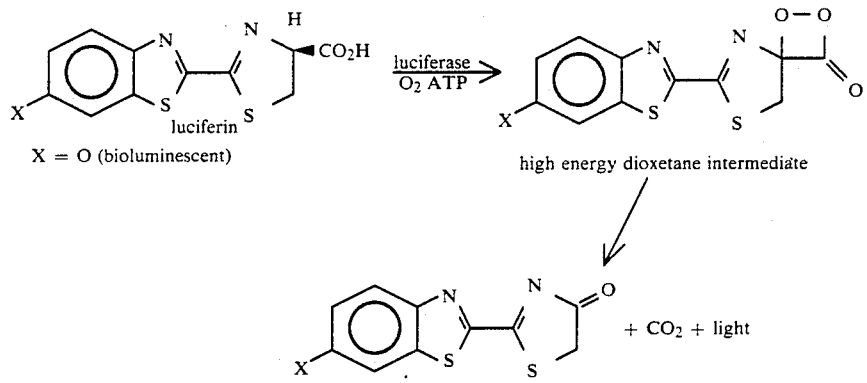

3. First Synthesis of Authentic 1,2-Dioxetanes. In 1969 Kopecky and Mumford reported the first synthesis of a dioxetane (3,3,4-trimethyl-1,2-dioxetane) by the base-catalyzed cyclization of a beta-bromohydroperoxide. (K. R. Kopecky and C. Mumford, *Can. J. Chem.*, 47, 709 (1969)). As predicted by McCapra, this dioxetane did, in fact, produce chemiluminescence upon heating to 50° C. with decomposition to acetone and acetaldehyde However, this peroxide is relatively unstable and cannot be stored at room temperature (25° C.) without rapid decomposition. In addition, the chemiluminescence efficiency is very low (less than 0.1%).

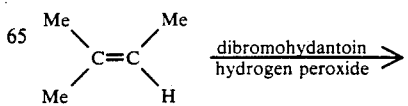

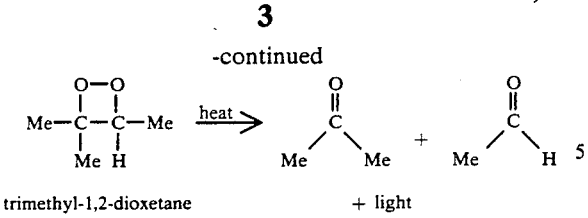

trimethyl-1,2-dioxetane + light

Bartlett and Schaap and Mazur and Foote independently developed an alternative and more convenient synthetic route to 1,2-dioxetanes. Photooxygenation of properly-substituted alkenes in the presence of molecular oxygen and a photosensitizing dye produces dioxetanes in high yields (P D. Bartlett and A. P. Schaap, *J. Amer Chem. Soc.*, 92, 3223 (1970) and S. Mazur and C. S. Foote, *J. Amer. Chem Soc.*, 92, 3225 (1970)). The mechanism of this reaction involves the photochemical generation of a metastable species known as singlet oxygen which undergoes 2+2 cycloaddition with the alkene to yield the dioxetane. Research has shown that a variety of dioxetanes can be prepared using this reaction (A. P. Schaap, P. A. Burns and K. A. Zaklika, *J. Amer. Chem. Soc.*, 99, 1270 (1977); K. A. Zaklika, P. A. Burns, and A. P. Schaap, *J. Amer. Chem. Soc.*, 100, 318 (1978); K. A. Zaklika, A. L. Thayer, and A. P. Schaap, *J. Amer. Chem. Soc.*, 100, 4916 (1978); K. A. Zaklika, T. Kissel, A. L. Thayer, P. A. Burns, and A. P. Schaap, *Photochem Photobiol.*, 30, 35 (1979); and A. P. Schaap, A. L. Thayer and K. Kees, *Organic Photochemical Synthesis*, II, 49 (1976)). During the course of this research, a polymer-bound sensitizer for photooxygenations was developed (A. P. Schaap, A. L. Thayer, E. C. Blossey, and D. C. Neckers, *J. Amer. Chem. Soc.*, 97, 3741 (1975); and A. P. Schaap, A. L. Thayer, K. A. Zaklika, and P. C. Valenti, *J. Amer. Chem. Soc.*, 101, 4016 (1979)). This new type of sensitizer has been patented and sold under the tradename SENSITOX ™ (U.S. Pat. No. 4,315,998 (2/16/82); Canadian Patent No. 1,044,639 (12/19/79)). Over fifty references have appeared in the literature reporting the use of this product.

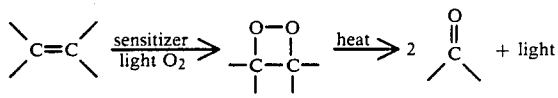

4. Preparation of Stable Droxetanes Derived from Sterically Hindered Alkenes. Wynberg discovered that photooxygenation of sterically hinderad alkenes such as adamantylideneadamantane affords a very stable dioxetane (J. H. Wieringa, J. Strating, H. Wynberg, and W. Adam, *Tetrahedron Lett.*, 169 (1972)). A collaborative study by Turro and Schaap showed that this dioxetane exhibits an activation energy for decomposition of 37 kcal/mol and a half-life at room temperature (25° C.) of over 20 years (N. J. Turro, G. Schuster, H. C. Steinmetzer, G. R. Faler, and A. P. Schaap, *J. Amer. Chem. Soc.*, 97, 7110 (1975)). In fact, this is the most stable dioxetane yet reported in the literature. Adam and Wynberg have recently suggested that functionalized adamantylideneadamantane 1,2-dioxetanes may be useful for biomedical applications (W. Adam, C. Babatsikos, and G. Cilento, *Z. Naturforsch.*, 39b, 679 (1984); H. Wynberg, E. W. Meijer, and J. C. Hummelen, In *Bioluminescence and Chemiluminescence*, M. A. DeLuca and W. D. McElroy (Eds ) Academic Press, New York, p. 687, 1981; and J. C. Hummelen, T. M. Luider, and H. Wynberg, *Methods in Enzymology*, 133B, 531 (1986)).

However, use of this extraordinarily stable peroxide for chemiluminescent labels requires detection temperatures of 150° to 250° C. Clearly, these conditions are unsuitable for the evaluation of biological analytes in aqueous media McCapra, Adam, and Foote have shown that incorporation of a spirofused cyclic or polycyclic alkyl group with a dioxetane can help to stabilize dioxetanes that are relatively unstable in the absence of this sterically bulky group (F. McCapra, I. Beheshti, A. Burford, R. A. Hann, and K. A. Zaklika, *J. Chem. Soc., Chem. Commun*, 944 (1977); W. Adam, L. A. A. Encarnacion, and K. Zinner, *Chem. Ber.*, 116, 839 (1983); G. G. Geller, C. S. Foote, and D. B. Pechman, *Tetrahedron Lett.*, 673 (1983); P. Lechtken, *Chem Ber.*, 109, 2862 (1976); and P. D. Bartett and M. S. Ho, *J. Amer. Chem. Soc.*, 96, 627 (1974))

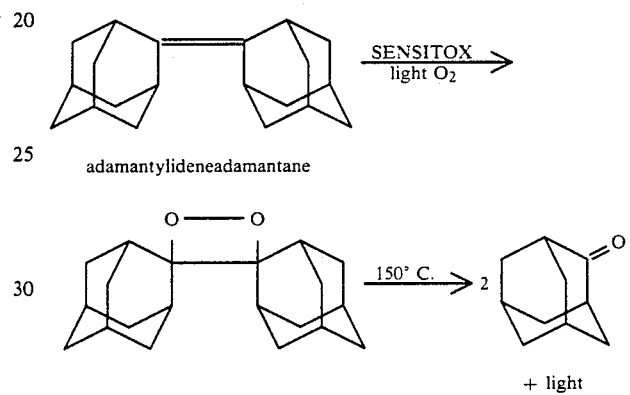

5. Effects of Substituents on Dioxetane Chemiluminescence. The stability and the chemiluminescence efficiency of dioxetanes can be altered by the attachment of specific substituents to the peroxide ring (K. A. Zaklika, T. Kissel, A. L. Thayer, P. A. Burns, and A. P. Schaap, *Photochem. Photobiol.*, 30, 35 (1979); A. P. Schaap and S. Gagnon, *J. Amer. Chem. Soc.*, 104, 3504 (1982); A. P. Schaap, S. Gagnon, and K. A. Zaklika, *Tetrahedron Lett.*, 2943 (1982); and R. S. Handley, A. J. Stern, and A. P. Schaap, *Tetrahedron Lett.*, 3183 (1985)). The results with the bicyclic system shown below illustrate the profound effect of various functional groups on the properties of dioxetanes. The hydroxy-substituted dioxetane (X=OH) derived from the 2,3-diaryl-1,4-dioxene exhibits a half-life for decomposition at room temperature (25° C.) of 57 hours and produces very low levels of luminescence upon heating at elevated temperatures. In contrast, however, reaction of this dioxetane with a base at $-30°$ C. affords a flash of blue light Kinetic studies have shown that the deprotonated dioxetane ($X=O^-$) decomposes $5.7 \times 10^6$ times faster than the protonated form (X=OH) at 25° C.

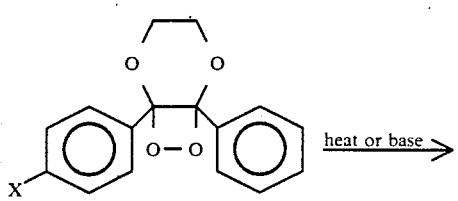

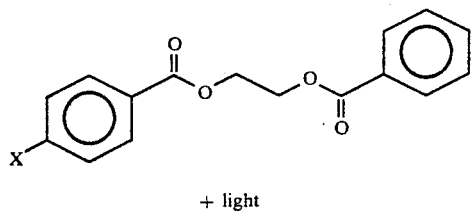

+ light

X=O⁻ (chemiluminescent)
X=OH (non-chemiluminescent)

The differences in the properties of these two dioxetanes arise because of two competing mechanisms for decomposition (K. A. Zaklika, T. Kissel, A. L. Thayer, P. A. Burns, and A. P. Schaap, *Photochem Photobiol.*, 30, 35 (1979); A. P. Schaap and S. Gagnon, *J. Amer. Chem. Soc.*, 104, 3504 (1982); A. P. Schaap, S Gagnon and K. A. Zaklika, *Tetrahedron Lett.*, 2943 (1982); and R. S. Handley, A. J. Stern and A. P. Schaap, *Tetrahedron Lett.*, 3183 (1985)). Most dioxetanes cleave by a process that involves homolysis of the O—O bond and formation of a biradical. An alternative mechanism is available to dioxetanes bearing substituents such as O⁻ with low oxidation potentials. The cleavage is initiated by intramolecular electron transfer from the substituent to the antibonding orbital of the peroxide bond.

6. Chemical Triggering of Dioxetanes. The first example in the literature is described above (A. P. Schaap and S. Gagnon, *J. Amer. Chem. Soc.*, 104, 3504 (1982)). However, the hydroxy-substituted dioxetane and any other examples of the dioxetanes derived from the diaryl-1,4-dioxenes are far too unstable to be of use in any application. They have half-lives at 25° C. of only a few hours Neither the dioxetane nor the precursor alkene would survive the conditions necessary to prepare derivatives. Further, these non-stabilized dioxetanes are destroyed by small quantities of amines (T. Wilson, *Int. Rev. Sci.: Chem.*, Ser. Two, 9, 265 (1976)) and metal ions (T. Wilson, M. E. Landis, A. L. Baumstark, and P. D. Bartlett, *J. Amer. Chem. Soc.*, 95, 4765 (1973); P. D. Bartlett, A. L. Baumstark, and M. E. Landis, *J. Amer. Chem. Soc.*, 96, 5557 (1974) and could not be used in the aqueous buffers required for enzymatic triggering.

7. Energy-Transfer Chemiluminescence Involving Dioxetanes in Homogeneous Solution. The first example of energy-transfer chemiluminescence involving dioxetanes was described by Wilson and Schaap (T. Wilson and A. P. Schaap, *J. Amer. Chem. Soc.*, 93, 4126 (1971)). Thermal decomposition of a very unstable dioxetane (cis-diethoxydioxetane) gave both singlet and triplet excited ethyl formate Addition of 9,10-diphenylanthracene and 9,10-dibromoanthracene resulted in enhanced chemiluminescence through singlet-singlet and triplet-singlet energy-transfer processes, respectively. These techniques have subsequently been used by many other investigators to determine yields of chemiexcited products generated by the thermolysis of various dioxetanes (For a review, see W. Adam, In *Chemical and Biological Generation of Excited States*, W. Adam and G. Cilento, Eds. Ch. 4, Academic Press, New York, 1982). Energy transfer in homogeneous solution, however, requires high concentrations of the energy acceptor because of the short lifetimes of the electronically excited species. These high concentrations lead to problems of self-quenching and reabsorption. The present invention solves the problem by using the 1,2-dioxetane and a fluorescent energy acceptor which are preferably both incorporated in a micelle affording efficient energy transfer without the need for high concentrations of a fluorescer in bulk solution.

8. Enhanced Chemiluminescence from a Dioxetane Using Intermolecular Energy in Micelles. Rates of various chemical reactions can be accelerated by micelles in aqueous solution (See, for example: E. H. Cordes and R. B. Dunlap, *Acc. Chem Res.*, 2, 329 (1969). Catalysis results from solubilization of the substrate in the micellar pseudophase and from electrostatic, tydrophobic, or polarity factors Aqueous micelles have been used to increase the rate of chemically triggered dioxetanes (A. P. Schaap, Final Technical Report to the Office of Naval Research, 1987, page 16). No experiments using fluorescent compounds such as co-surfactants to enhance chemiluminescence efficiency are reported.

Several reports describe enhanced chemiluminescence from chemical reactions in micellar environments. However, none of these make use of energy transfer to a fluorescent co-surfactant No stabilized dioxetanes have been studied in micelles Goto has investigated the chemical oxidation of a luciferin in the presence of neutral, anionic, and cationic surfactants (T. Goto and H. Fukatsu, *Tetrahedron Lett.*, 4299 (1969)). The enhanced chemiluminescence was attributed to an increase in the fluorescence efficiency of the reaction product in the micelle compared to aqueous solution. The effect of cetyltrimethylammonium bromide micelles on the chemiluminescent reaction of acridan esters in aqueous alkaline solution has been reported (F. McCapra, *Acc. Chem. Res.*, 9, 201 (1976). McCapra indicates, however, that micellar environment does not "assist the excitation reaction". Rather, the micelles are thought to enhance the luminescent yield by decreasing the rate of a competing, non-luminescent hydrolytic reaction. Similarily, Nikokavouras and Gundermann have studied the effect of micelles on chemiluminescent reactions of lucigenin and luminol derivatives, respectively (C. M. Paleos, G. Vassilopoulos, and J. Nikokavouras, *Bioluminescence and Chemiluminescence*, Academic Press, New York, 1981, p. 729; K. D. Gundermann, Ibid., p. 17). Shinkai observed that chemiluminescence yields from unstable, non-isolable dioxetanes could be enhanced in micelles relative to water (S. Shinkai, Y. Ishikawa, O. Manabe, and T. Kunitake, *Chem Lett*, 1523 (1981). These authors suggested that the yield of excited states may be higher in the hydrophobic core of micelles than in water.

The only reference to enhancement of enzymatically generated chemiluminescence with surfactants involves the work of Kricka and DeLuca on the firefly luciferase system (L J Kricka and M. DeLuca, *Arch. Biochem. Biophys.*, 217, 674 (1983)). Nonionic detergents and polymers enhanced the total light yield by increasing the turnover of the enzyme Cationic surfactants such as (cetyltrimethylammonium bromide, CTAB) actually resulted in complete inhibition of the catalytic activity of the luciferase.

A method for enhancing the chemiluminescent yield of the luminol/peroxidase reaction by addition of 6-hydroxybenzothiazole derivatives or para-substituted phenols (G. H. G. Thorpe, L. J. Kricka, S. B. Moseley, T. P. Whitehead, *Clin. Chem.*, 31, 1335 (1985); G. H. G. Thorpe and L. J. Kricka, *Methods in Enzymology*, 133, 331 (1986); and L. J. Kricka, G. H. G. Thorpe, and R. A. W. Stott, *Pure & Appl. Chem.*, 59, 651 (1987)). The mechanism for the enhancement is not known but it does not involve intramolecular energy transfer or intermolecular transfer to a co-micellar fluorescent surfactant.

Co-micellar fluorescent probes have been used to study the dynamic properties of micelles (Y. Kubota, M. Kodama, and M. Miura, Bull. Chem. Soc.. Jpn., 46, 100 (1973); N. E. Schore and N J. Turro, *J. Amer. Chem Soc.*, 6, 306 (1974); and G. W. Pohl, *Z. Naturforsch*, 31c, 575 (1976)). However, no examples appear in the literature of using these fluorescent materials to enhance chemiluminescent reactions in micelles through energy-transfer processes.

9. Chemiluminescent Immunoassays. There are no reports of dioxetanes as enzyme substrates or their use in enzyme-linked assays prior to the filing date of Serial No. 87,139. Wynberg has used stable dioxetanes as "thermochemiluminescent" labels for immunoassays (J. C. Hummelen, T. M. Luider, and H. Wynberg, *Methods in Enzymology*, 133B, 531 (1986)). These dioxetanes are used to label biological materials such as proteins. Assays are subsequently conducted by heating the sample at 100° to 250° C. and detecting the thermally generated chemiluminescence. This technique is distinctly different from the use of triggerable dioxetanes as enzyme substrates.

Luminol derivatives, acridinium esters and lucigenin have been employed as chemiluminescent labels for antigens, antibodies, and haptens (H. R. Schroeder and F. M. Yeager, *Anal. Chem.*, 50, 1114 (1978); H. Arakawa, M. Maeda, and A. Tsuju, *Anal. Biochem*, 79, 248 (1979); and H. Arakawa, M. Maeda, and A. Tsuji, *Clin. Chem.*, 31, 430 (1985). For reviews, see L. J. Kricka and T. J. N. Carter, *In Clinical and Biochemical Luminescence*, L. J. Kricka and T. J. N. Carter (Eds.), Marcel Dekker, Inc., New York , 1982, Ch. 8; L. J. Kricka, *Ligand-Binder Assays*, Marcel Dekker, Inc., New York, 1985, Ch. 7; F. McCapra and I. Beheshti, In *Bioluminescence and Chemiluminescence: Instruments and Applications*, Vol. I, K. Van Dyke (Ed.), CRC Press, Inc., Boca Raton, Fla., 1985, Ch. 2, Note, in particular, the section on dioxetanes, p. 13; and G. J. R. Barnard, J. B. Kim, J. L. Williams, and W. P. Collins, *Ibid*, Ch. 7). Assay systems involving the use of enzyme-labeled antigens, antibodies, and haptens have been termed enzyme immunoassays. The enzyme labels have been detected by color or fluorescence development techniques. More recently, luminescent enzyme immunoassays have been based on peroxidase conjugates assayed with luminol/-hydrogen peroxide, pyrogallol/hydrogen peroxide, *Pholas dactylus* luciferin, or luminol under alkaline conditions (L. J. Kricka and T. J. N. Carter, In *Clinical and Biochemical Luminescence*, L. J. Kricka and T. J. N. Carter (Eds.), Marcel Dekker, Inc , New York, 1982, Ch. 8). No enzyme-linked assays have described dioxetanes as enzymatic substrates to generate light for detection prior to my application Serial No. 887,139.

10. Photographic Detection of Luminescent Reactions. Instant photographic film and x-ray film have been used to record light emission from several chemiluminescent and bioluminescent reactions (L. J. Kricka and G. H. G. Thorpe, *Methods in Enzymology*, 133, 404 (1986) and references therein See also: M. M. L. Leong, C. Milstein, and R. Pannel, J. Histochem. *Cytochem*, 34, 1645 (1986); R. A. Bruce, G. H. G. Thorpe, J. E. C. Gibbons, P. R. Killeen, G. Ogden, L. J. Kricka, and T. P. Whitehead, *Analyst*, 110, 657 (1985); J. A. Matthews, A. Batki, C. Hynds, and L. J. Kricka, *Anal. Biochem* , 151, 205 (1985); and G. H. G. Thorpe, T. P. Whitehead, R. Penn, and L. J. Kricka, *Clin. Chem.*, 30, 806 (1984). No examples appear in the literature on the photographic detection of chemiluminescence derived from chemical or enzymatic triggering of stabilized dioxetanes prior to my application Serial No. 887,139.

OBJECTS

It is therefore an object of the present invention to provide a method and compositions for enhancing the chemiluminescence of triggerable 1,2-dioxetanes Further, it is an object of the present invention to provide a method and compositions which can be used in immunoassays and with enzyme linked DNA probes. These and other objects will become increasingly apparent by reference to the following description and the drawings.

IN THE DRAWINGS

Figure 6:
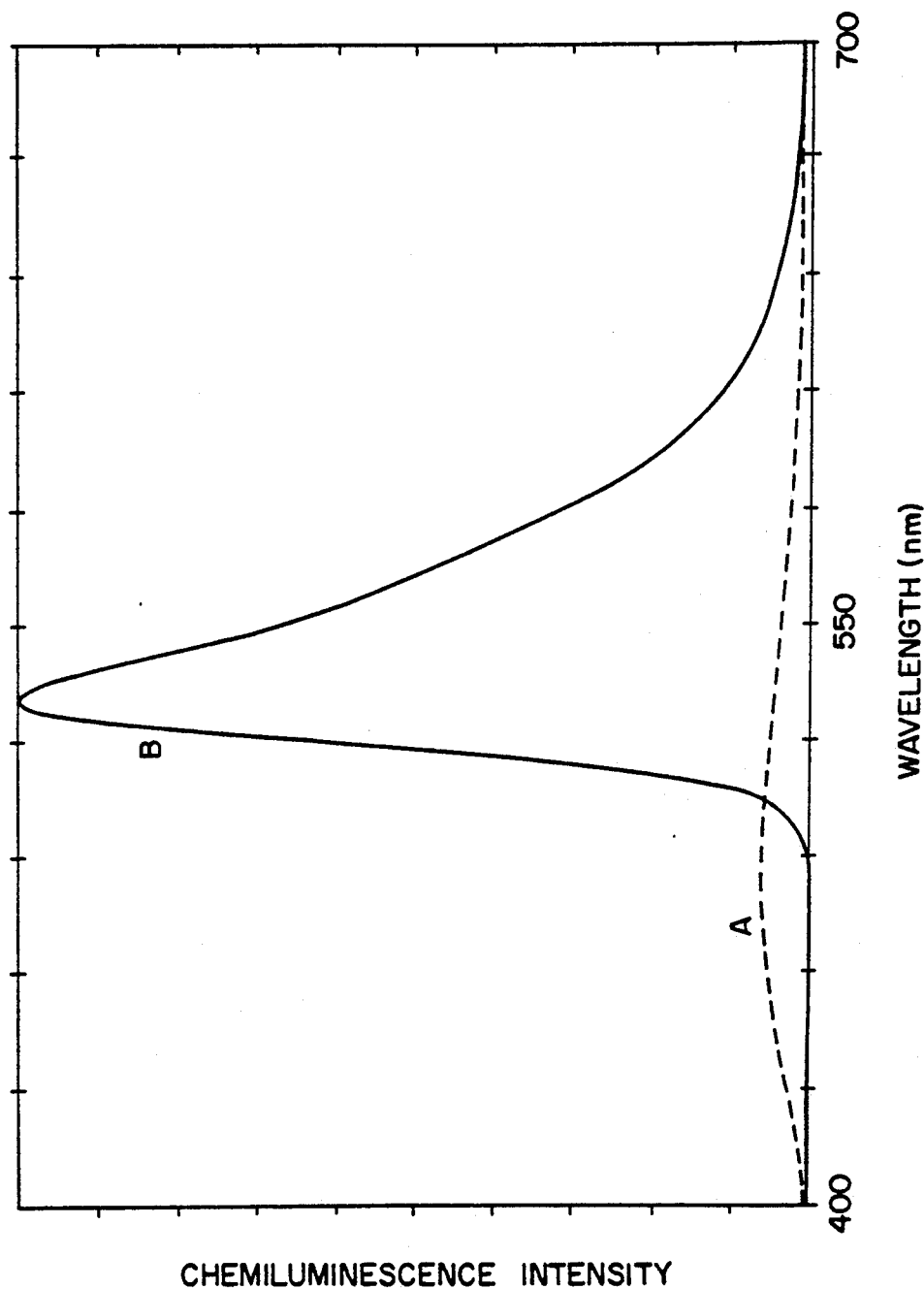

FIG. 6 shows chemiluminescence spectra: (Curve A) chemiluminescence from enzymatic triggering of dioxetane 2c in 221 buffer in the absence of CTAB and fluorescent co-surfactant 3; (Curve B) energy-transfer chemiluminescence from enzymatic triggering of dioxetane 2c in the presence of CTAB and 3.

Figure 7:
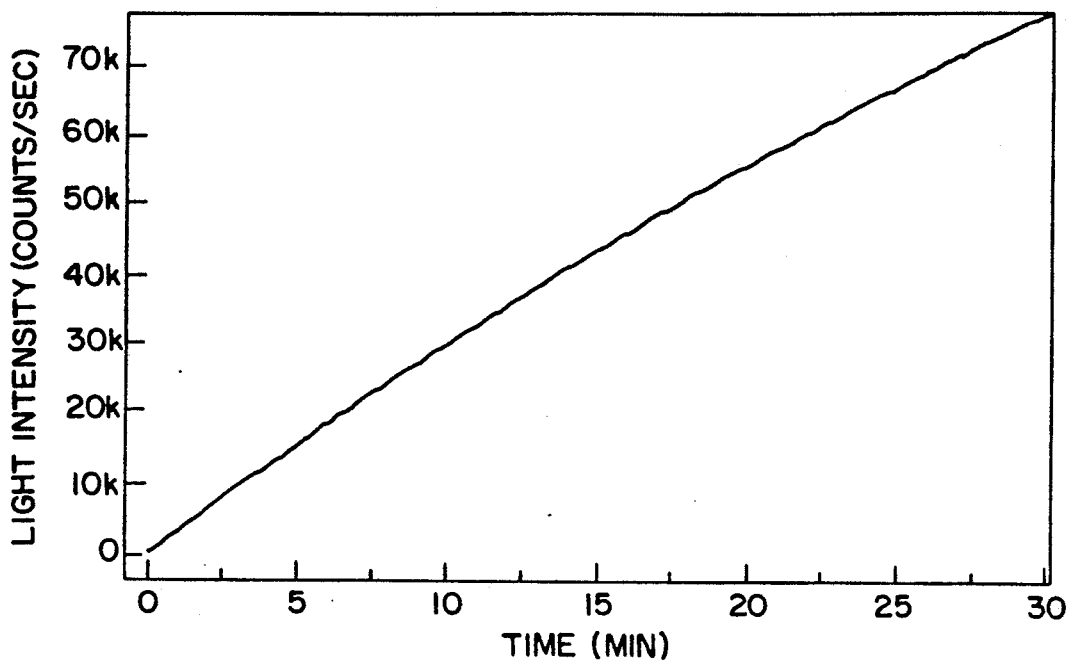

FIG. 7 shows a plot of light intensity vs. time for dioxetane 2c in 3 mL of 221 buffer with CTAB/-fluorescer and $2.7 \times 10^{-15}$ moles of alkaline phosphatase (Experiment D). Reagent background in the absence of enzyme is equal to intensity at time zero.

Figure 8:
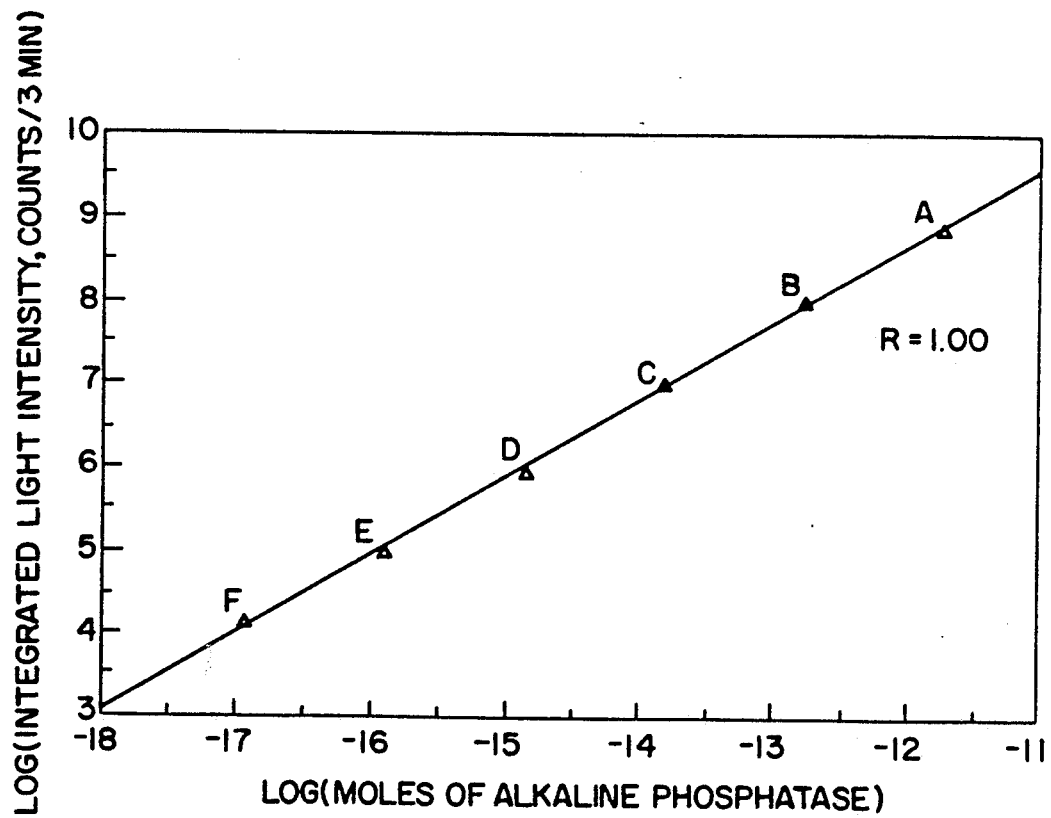

FIG. 8 shows plot of log (integrated light intensity) for time period of zero to 3 minutes vs. log (moles of alkaline phosphatase).

Figure 9:
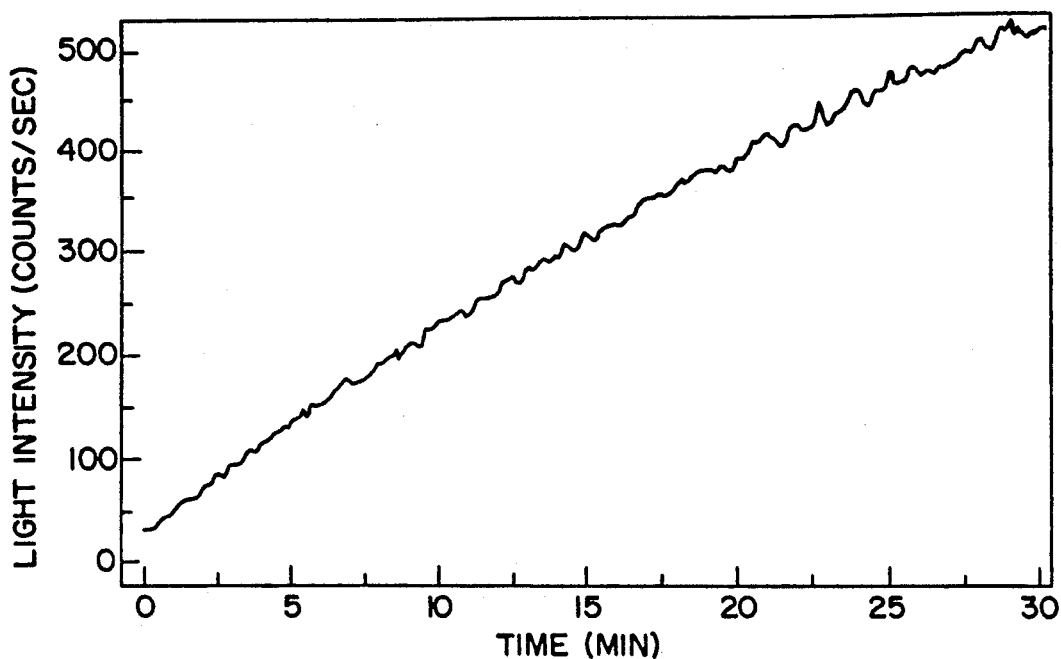

FIG. 9 shows a plot of light intensity vs. time for dioxetane 2c in 200 microliters of 221 buffer with CTAB/fluorescer and $2.3 \times 10^{-17}$ moles of alkaline phosphatase. Reagent background in the absence of enzyme is equal to the intensity at time zero.

Figure 10:
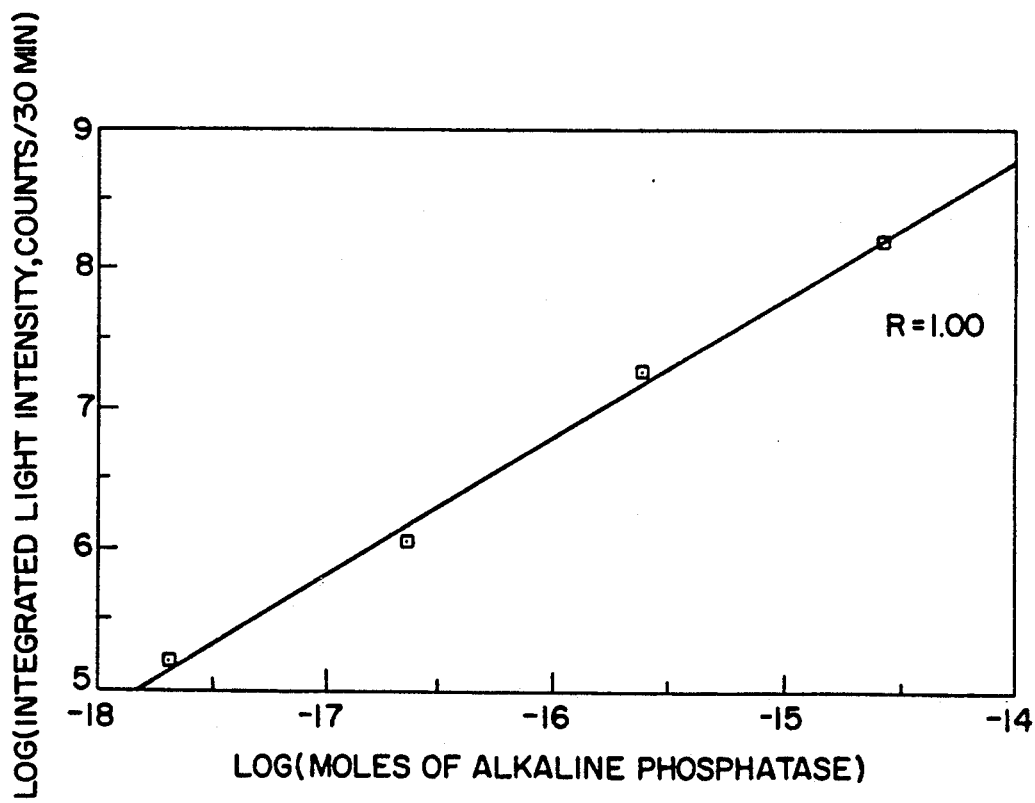

FIG. 10 shows a plot of log (integrated light intensity) for time period of zero to 30 minutes vs. log (moles of alkaline phosphatase).

Figure 11:
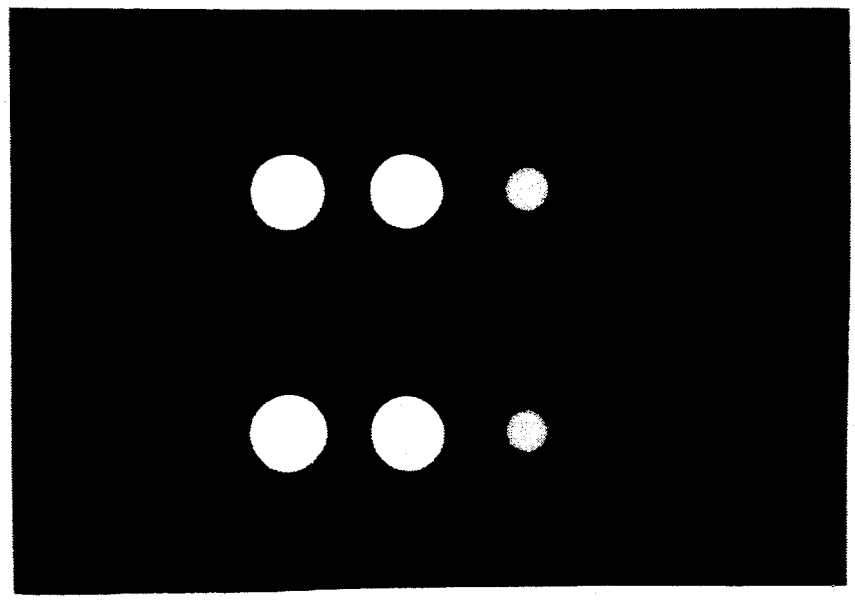

FIG. 11 is a photographic detection of chemiluminescence from dioxetane 2c using ASA 3000 Polaroid Type 57 film. Solutions of 221 buffer (100 microliters) containing alkaline phosphatase, dioxetane, $Mg(OAc)_2$, CTAB, and fluorescein surfactant 3 were incubated in Dynatech Immulon TM wells for 1 hour at 37° C. and then photographed at that temperature for 15 minutes. Quantitites of alkaline phosphatase: A, 2700 attomol; B, 250 attomol; C, 23 attomol; and D, reagent control with no enzyme (not visible).

Figure 12:
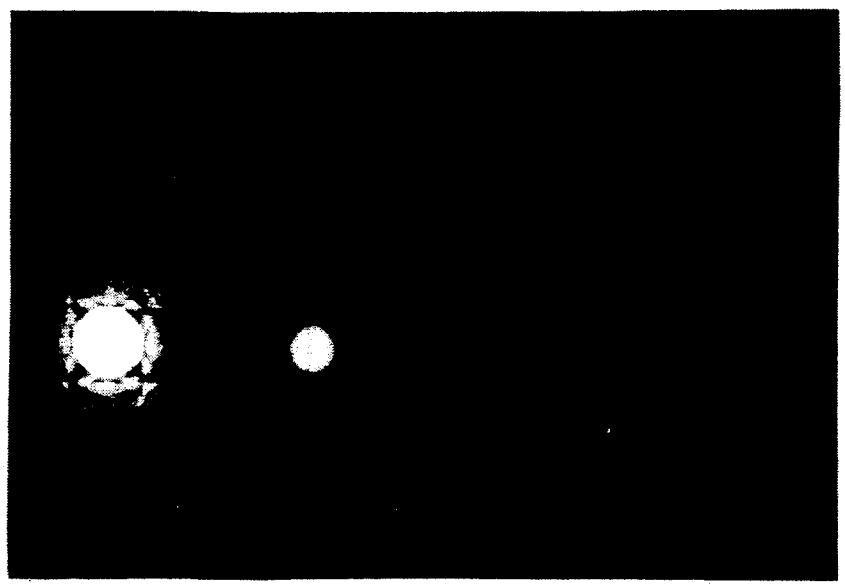

FIG. 12 is a photographic detection of chemiluminescence from dioxetane 2c using ASA 3000 Polaroid Type 57 film Solutions of 221 buffer (100microliters) containing alkaline phosphatase, dioxetane, Mg(OAc)$_2$, CTAB, and fluorescein surfactant 3 were incubated in Dyntech Immulon ™ wells for 1 hour at 37° C. and then photographed at that temperature for 30 minutes Quantities of alkaline phosphatase: A, 250 attomol; B, 23 attomol; C, 2 attomol; and D, reagent control with no enzyme (not visible).

Figure 13:
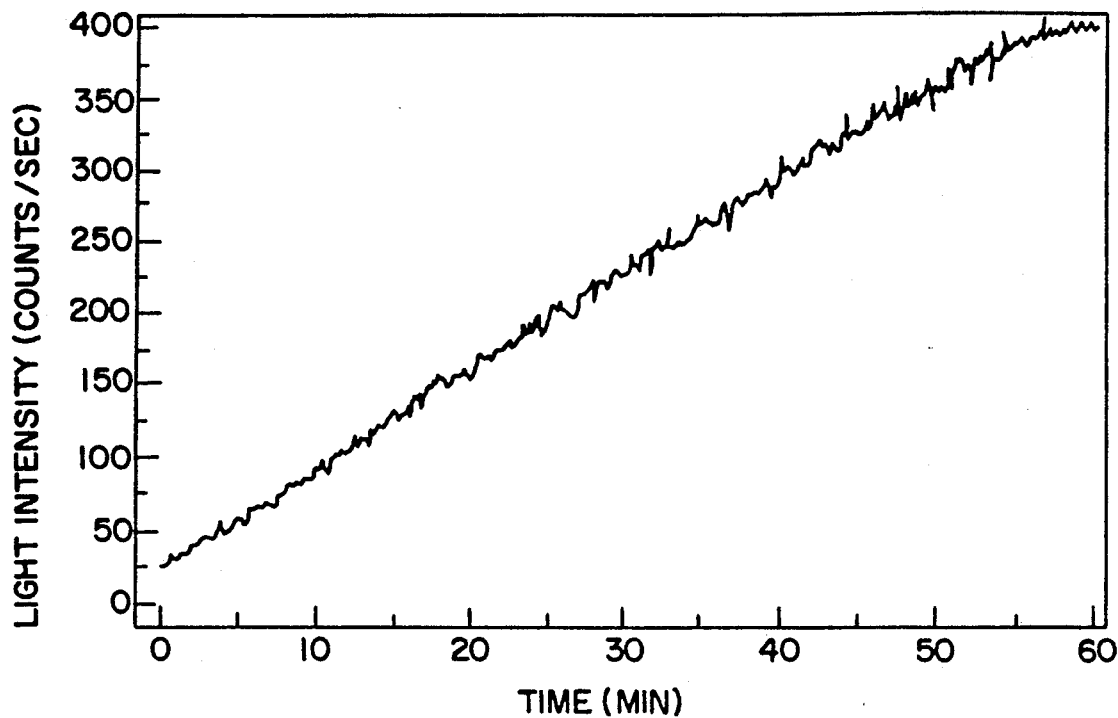

FIG. 13 shows a plot of light intensity vs. time for dioxetane 2c in 100 microliters of 221 buffer with CTAB/fluorescer and 1.3 ng S-antigen and antibody-alkaline phosphatase conjugate. Reagent background in the absence of enzyme is equal to the intensity at time zero.

Figure 14:
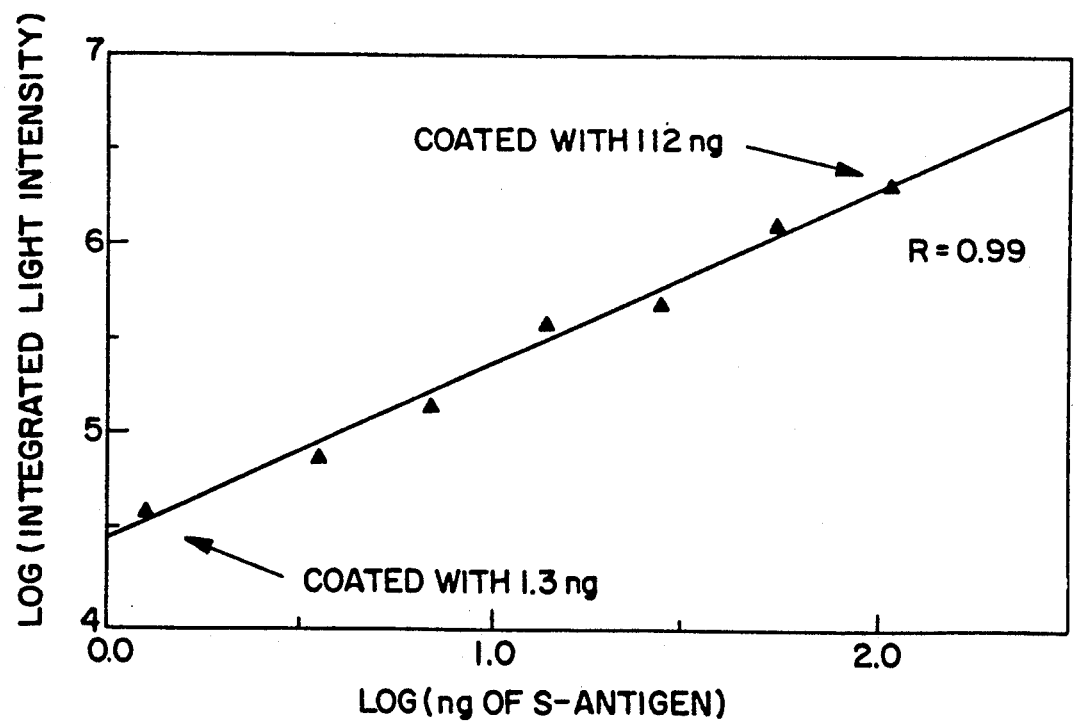

FIG. 14 shows a plot of log (integrated light intensity) for time period of zero to 15 minutes vs. log (ng of S-antigen coated on the microwell).

Figure 15:
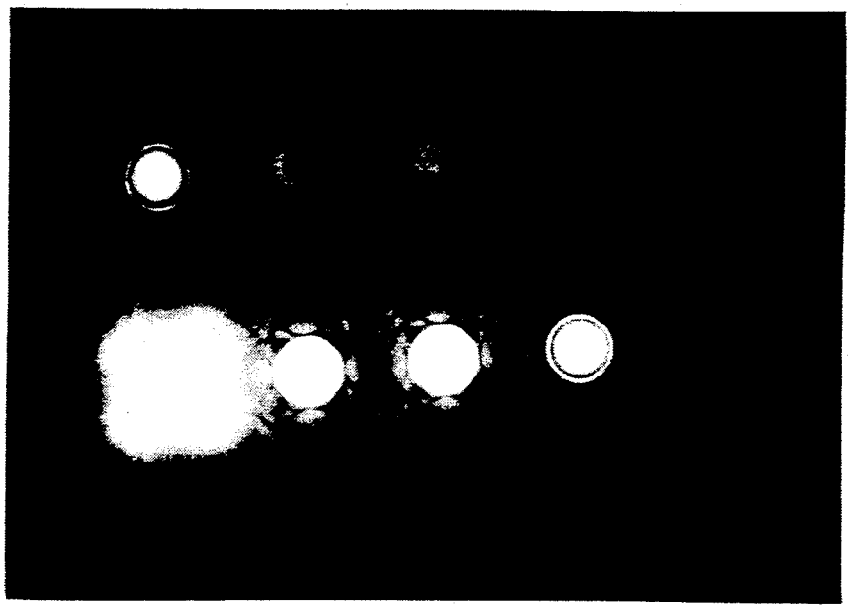

FIG. 15 is a chemiluminescent assay for S-antigen using dioxetane 2c, Mg(OAc)$_2$, CTAB, and fluorescein surfactant 3 in 221 buffer (100 microliters). Following the luminometer experiments the 7 Immulon ™ wells were incubated for 30 minutes at 37° C. and then photographed at that temperature for 15 minutes with ASA 3000 Polaroid Type 57 film. Quantities of S-antigen from lower left to second from upper right: 112, 56, 28, 14, 7, 3.5, and 1.3 ng with well containing only reagents in upper right (not visible).

Figure 16:
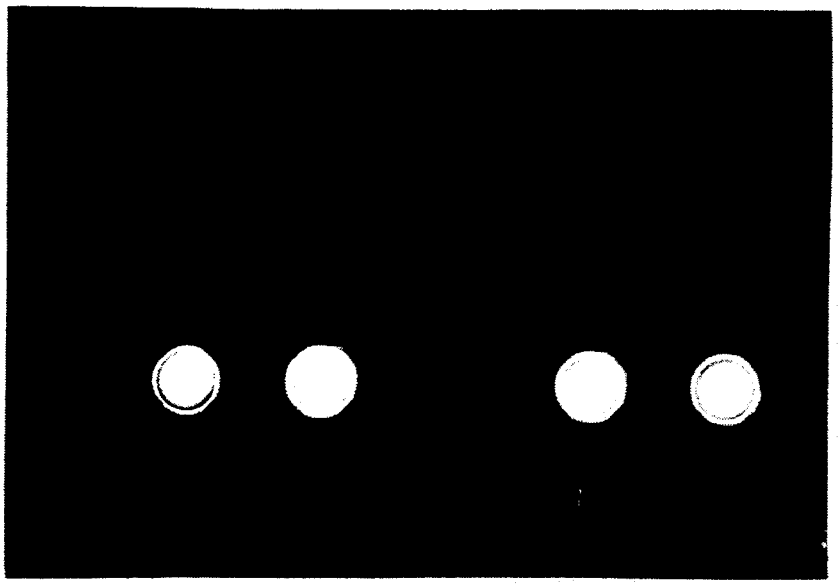

FIG. 16 is a chemiluminscent assay for S-antigen. Four wells were coated with 50 ng of S-antigen, reacted with MAbA9-C6 monoclonal antibody, reacted with antimouse IgG-alkaline phosphatase conjugate, and then assayed with dioxetane 2c, Mg(OAc)$_2$, CTAB, and fluorescein surfactant 3 in 221 buffer (100 microliters). The wells were incubated for 1 hour at 45° C. and then photographed at that temperature for 30 seconds with ASA 3000 Polaroid Type 57 film. A control well in the center (not visible) contained only the dioxetane in the CTAB/fluorescein buffer.

GENERAL DESCRIPTION

The present invention relates to a method for generating light which comprises providing a fluorescent compound in closely spaced relationship with a stable 1,2-dioxetane compound of the formula

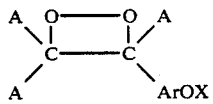

wherein ArOX is an aryl group having an aryl ring substituted with an X-oxy group which forms an unstable oxide intermediate 1,2-dioxetane compound when triggered to remove X by an activating agent so that the unstable 1,2-dioxetane compound decomposes and releases electronic energy to form light and two carbonyl containing compounds of the formula

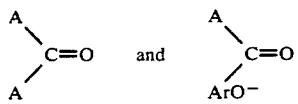

wherein X is a chemically labile group which is removed by the activating agent to form the unstable oxide intermediate 1,2-dioxetane and wherein A are passive organic groups which allow the light to be produced and decomposing the stable 1,2-dioxetane with the activating agent wherein the fluorescent compound accepts the electronic energy generated upon decomposition of the unstable oxide intermediate and produces a more intense light than is produced by the triggering of the dioxetane alone.

In particular the present invention relates to a method for generating light which comprises providing a fluorescent compound in closely spaced relationship with a stable 1,2-dioxetane compound of the formula

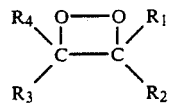

wherein R$_1$ and R$_2$ together and R$_3$ and R$_4$ together can be joined as spirofused alkylene groups which can contain hetero atoms (N, S, O or P) and aryl rings, wherein at least one of R$_1$ and R$_2$ or R$_3$ and R$_4$ is an aryl group, having an aryl ring substituted with an X oxy- group which forms an unstable oxide intermediate 1,2-dioxetane compound when triggered to remove X by an activating agent selected from acids, bases, salts, enzymes, inorganic and organic catalysts and electron donors so that the unstable 1,2-dioxetane compound decomposes and releases electronic energy to form light and two carbonyl containing compounds of the formula:

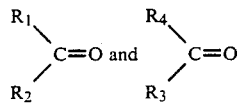

wherein those of R$_1$, R$_2$, R$_3$ or R$_4$ which are unsubstituted by an X-oxy group are carbon or hetero atom containing organic groups which provide stability for the stable 1,2-dioxetane compound and wherein X is a chemically labile group which is removed by the activating agent to form the unstable oxide intermediate; and decomposing the stable 1,2-dioxetane with the activating agent wherein the fluorescent compound accepts the electronic energy generated upon decomposition of the unstable oxide intermediate and produces a more intense light than is produced by the triggering of the dioxetane alone.

The present invention also relates to compositions which generate light upon triggering which comprises a fluorescent compound and a stable 1,2-dioxetane of the formula

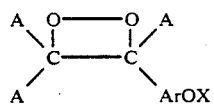

wherein ArOX represents an aryl group substituted with an X-oxy group which forms an unstable oxide intermediate 1,2-dioxetane compound when triggered to remove X by an activating agent so that the unstable 1,2-dioxetane compound decomposes and releases electronic energy to form light and two carbonyl containing compounds of the formula

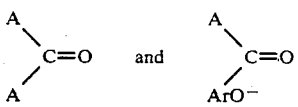

wherein X is a chemically labile group which is removed by the activating agent to form the unstable oxide intermediate 1,2-dioxetane and wherein A are passive organic groups which allow the light to be produced wherein the stable 1,2-dioxetane is decomposed with the activating agent and wherein the fluorescent compound accepts the electronic energy generated upon decomposition of the unstable oxide intermediate and produces a more intense light than is produced by the triggering of the dioxetane alone.

The compositions use the same preferred dioxetanes as the method.

Further the present invention relates to a method for generating light which comprises providing a fluorescent compound in closely spaced relationship with a stable dioxetane compound of the formula:

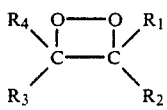

wherein $R_1$ is selected from alkyl, alkoxy, aryloxy, dialkyl or aryl amino, trialkyl or aryl silyloxy and aryl groups including spirofused aryl groups with $R_2$, wherein $R_2$ is an aryl group which can include $R_1$ and is substituted with an X-oxy group which forms an unstable oxide intermediate 1,2-dioxetane compound when activated by an activating agent to remove X selected from acids, bases, salts, enzymes, inorganic and organic catalysts and electron donors so that the unstable 1,2-dioxetane compound decomposes and releases electronic energy to form light and two carbonyl containing compounds of the formula:

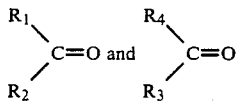

wherein X is a chemically labile group which is removed by the activating agent to form the unstable oxide intermediate and wherein $R_3$ and $R_4$ are selected from aryl, heteroalkyl and alkyl groups which can be joined together as spirofused polycyclic alkyl and polycyclic aryl groups and decomposing the stable 1,2-dioxetane with the activating agent wherein the fluorescent compound accepts the electronic energy generated upon decomposition of the unstable oxide intermediate and produces a more intense light than is produced by the triggering of the dioxetane alone.

Any fluorescent compound which has a lower energy for its singlet excited states compared to the excited state of the dioxetane product can be used to enhance the chemiluminescence efficiency. A group such as a long hydrocarbon chain (preferably 8 to 20 carbon atoms) is preferably attached to the fluorescer so that it acts as a co-surfactant in order to incorporate the material into the organized assembly Examples of fluorescers include: any fluorescent dye; aromatic compounds including naphthalenes, anthracenes, pyrenes, biphenyls; acridine; coumarins; xanthenes; phthalocyanines; stilbenes; furans; oxazoles; oxadiazoles; and benzothiazoles. Most preferably a surfactant which forms micelles with the fluorescent compound is used so that the 1,2-dioxetane is adjacent to the fluorescent compound Possible surfactants are described in Chapter 1, pages 1 to 18 of *Catalysis in Micellar and Macromolecular Systems* published by Academic Press, (1975). These include: zwitterion; cationic (ammonium, pyridinium, phosphonium, sulfonium salts); anionic (sulfate, sulfonate, carboxylate salts); neutral (polyoxyethylene derivatives, cyclodextrins, long chain esters, long chain amides); and naturally occurring surfactants (lipids).

Specifically the present invention relates to a method and compositions which use a stable 1,2-dioxetane compound of the formula:

wherein $R_1$ is selected from lower alkyl containing 1 to 8 carbon atoms, $R_2$ is selected from aryl, biaryl and fused ring polycyclic aryl groups which can be substituted or unsubstituted, and $R_3C-$ is selected from polycyclic alkyl groups containing 6 to 30 carbon atoms, wherein OX is an oxy group substituted on an aryl ring which forms an unstable oxide intermediate 1,2-dioxetane compound when triggered to remove X by an activating agent selected from acid, base, salt, enzyme, inorganic and organic catalysts and electron donor sources and X is a chemically labile group which is removed by the activating agent to form the unstable oxide intermediate and wherein (I) decomposes in the presence of an activating agent to produce light and carbonyl containing compounds of the formula

and

Also the present invention relates to a method and compositions which uses a stable, 1,2-dioxetane compound of the formula:

wherein ArOX is a spirofused aryl group containing a ring substituted X-oxy group, wherein ArOX forms an unstable oxide intermediate 1,2-dioxetane compound when triggered by an activating agent to remove X selected from acids, bases, salts, enzymes, inorganic and organic catalysts and electron donors, wherein X is a chemically labile group which is removed by the activating agent to form the unstable oxide intermediate 1,2-dioxetane so that the unstable 1,2-dioxetane compound decomposes to form light and two carbonyl containing derivatives of the formula $R_3C=O$ and $-OArC=O$ and wherein $R_3C-$ is selected from polycyclic alkyl groups containing 6 to 30 carbon atoms In this structure $R_1$ and $R_2$ are joined together.

In reference to the structure:

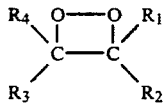

(1) When $R_1$ is not combined with $R_2$ the group is preferably alkyl, alkoxy, dialkyl or arylamino trialkyl or aryl silyloxy. The alkyl groups preferably contain 1 to 8 carbon atoms. $R_1$ can also be cyclic aliphatic or aryl groups, including fused ring aryl compounds, containing 6 to 14 carbon atoms. When $R_1$ is combined with $R_2$ they provide an aryl group containing 6 to 30 carbon atoms.

(2) $R_2$ is an aryl group substituted with an X oxy (OX) group. The aryl containing group can be phenyl, biphenyl, fused phenyl and other aryl groups and can contain between 6 and 30 carbon atoms and can include other substituents. X is any labile group which is removed by an activating agent. The OX group can be for instance selected from hydroxyl, alkyl or aryl carboxyl ester, inorganic oxy acid salt, particularly a phosphate or sulfate, alkyl or aryl silyloxy and oxygen pyranoside groups.

(3) $R_3$ and $R_4$ can be the same as $R_1$. In the following Examples, $R_3$ and $R_4$ are combined together to form a polycyclic alkylene group, particularly for ease of synthesis and comparison; however any organic group can be used. Preferably the polycyclic alkylene group contains 6 to 30 carbon atoms.

The stable 1,2-dioxetane compounds have relatively long ½ lives at room temperatures (20°-35° C.) even though they can be triggered by the activating agent. All of the prior art compounds are either unstable at room temperatures or require temperatures of 50° C or above in order to be thermally decomposed which is impractical for most applications.

The activating agent may be chemical or enzymatic. In some cases (F$^-$) 1 equivalent is required and in others (enzymatic) only a very small amount is used. The agents are described in any standard chemical treatise on the subject and include acids, bases, salts, enzymes and other inorganic, organic catalysts. The agent used will depend upon the conditions under which the stable 1,2-dioxetane is to be activated and how labile the X group is on a particular 1,2-dioxetane. Electron donors can be used to remove X which can include reducing agents as well as electrical sources of electrons.

The 1,2-dioxetane decomposes to form carbonyl containing compounds and light. An unstable 1,2-dioxetane intermediate is formed of the formula:

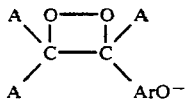

In general an $-ArOX$ substituted 1,2-dioxetanes are formed by addition of oxygen to the appropriate alkene. These alkenes are synthesized through alkyl and/or aryl substituted carbonyl containing compounds of the formula:

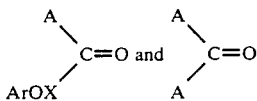

These materials are reacted in the presence of lithium aluminum hydride or other metal hydride in a polar organic solvent, particularly tetrahydrofuran, with a transition metal halide salt, particularly titanium chloride, and a tertiary amine base. The reaction is generally conducted in refluxing tetrahydrofuran and usually goes to completion in about 4 to 24 hours.

Preparation of and Chemical Triggering of Stabilized 1,2-Dioxetanes. It was discovered that thermally stable dioxetanes can be triggered by chemical and enzymatic processes to generate chemiluminescence on demand (A. P. Schaap, patent application Serial No. 887,139 filed Jul. 17, 1986, A. P. Schaap, R. S. Handley, and B. P. Giri, *Tetrahedron Lett.*, 935 (1987); A. P. Schaap, T. S. Chen, R. S. Handley, R. DeSilva, and B. P. Giri, *Tetrahedron Lett.*, 1155 (1987); and A. P. Schaap, M. D. Sandison, and R. S Handley, *Tetrahedron Lett.*, 1159 (1987)). To do this, new synthetic procedures were developed to produce dioxetanes with several key features: (1) the stabilizing influence of spirofused adamantyl groups has been utilized to provide dioxetanes that have "shelf lives" of years at ambient temperature; (2) a moiety has been incorporated in the structure so that direct chemiluminescence from the carbonyl cleavage product is obtained; and (3) new methods for triggering the chemiluminescent decomposition of the stabilized dioxetanes were provided.

The required alkenes have teen prepared by reaction of 2-adamantanone with aromatic esters or ketones using titanium trichloride/LAH in THF (A. P. Schaap, patent application Serial No. 887,139, filed Jul. 17, 1986). This is the first report of the intermolecrlar condensation of ketones and esters to form vinyl ethers using the McMurry procedure. Although McMurry had earlier investigated the intramolecular reaction of ketone and ester functional groups, cyclic ketones and not vinyl ethers were prepared by this method (J. E. McMurry and D. D. Miller, *J. Amer. Chem. Soc.*, 105, 1660 (1983)).

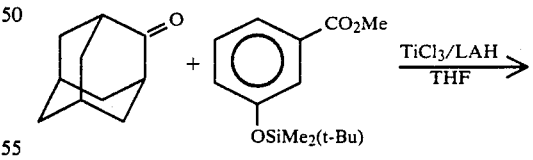

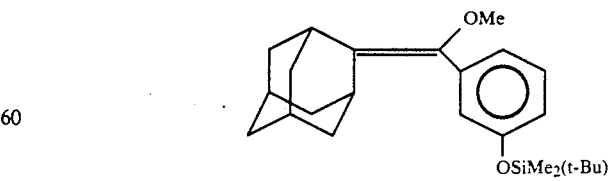

Photooxygenation of these vinyl ethers affords dioxetanes that are easily handled compounds with the desired thermal stability For example, the dioxetane shown below exhibits an activation energy of 28.4 kcal/mol and a half-life at 25° C. of 3.8 years. Samples of this dioxetane in o-xylene have remained on the laboratory bench for several months with no detectable decomposition.

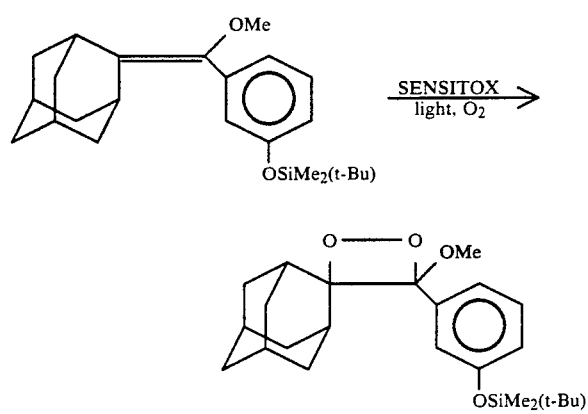

However, the chemiluminescent decomposition of this dioxetane can be conveniently triggered at room temperature by removal of the silyl-protecting with fluoride ion to generate the unstable, aryloxide form which cleaves to yield intense blue light. The half-life of the aryloxide-substituted dioxetane is 5 seconds at 25° C. The spectrum of the chemiluminescence in DMSO exhibited a maximum at 470 nm which is identical to the fluorescence of the anion of the ester cleavage product (methyl 3-hydroxylbenzoate) and the fluorescence of the spent dioxetane solution under these conditions. No chemiluminescence derived from adamantanone fluorescence appears to be produced Chemiluminescence quantum yields for the fluoride-triggered decomposition measured relative to the luminol standard was determined to be 0.25 (or a chemiluminescence efficiency of 25%). Correction for the fluorescence quantum yield of the ester under these conditions ($\Phi_F=0.44$) gave an efficiency for the formation the singlet excited ester of 57%, the highest singlet chemiexcitation efficiency yet reported for a dioxetane prepared in the laboratory.

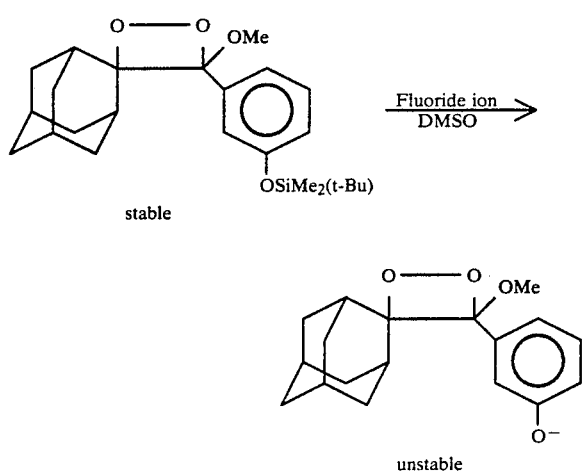

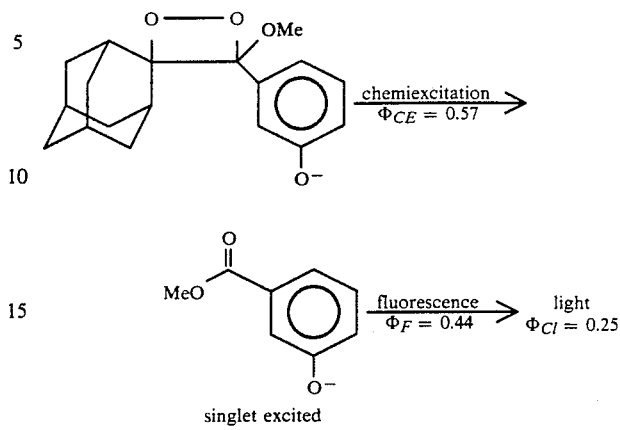

Enzymatic Triggering of 1,2-Dioxetanes. Biological assays such as immunoassays and nucleic acid probes involving enzymes utilize a wide variety of substrates which either form a color (chromogenic) or become fluorescent (fluorogenic) upon reaction with the enzyme. U.S. Pat. Application Ser. No. 887,139 describes the first dioxetanes which can function as chemiluminescent enzyme substrates (A. P. Schaap, patent application filed Jul. 17, 1986; A. P. Schaap, R. S. Handley, and B. P. Giri, Tetrahedron Lett., 935 (1987); A. P. Schaap, T. S. Chen, R. S. Handley, R. DeSilva, and B. P. Giri, Tetrahedron Lett., 1155 (1987); and A. P. Schaap, M. D. Sandison, and R. S. Handley, Tetrahedron Lett., 1159 (1987)). Use of these peroxides in biological systems requires dioxetanes which are thermally stable at the temperature of the enzymatic reaction and dont undergo rapid spontaneous decomposition in the aqueous buffers. The spirofused adamantyl dioxetanes described in the previous paragraph meet these requirements. 1,2-dioxetanes were prepared bearing functional groups which can be enzymatically modified to generate the aryloxide form. Decomposition of this unstable intermediate provides the luminescence. 1,2-dioxetanes were synthesized which can be triggered by various enzymes including aryl esterase, acetylcholinesterase, and alkaline phosphatase. The phosphatase example is particularly significant because this enzyme is used extensively in enzyme-linked immunoassays and nucleic acid probes.

For example, enzymatic triggering by alkaline phosphatase was observed with the phosphate-substituted 1,2-dioxetane derived from 3-hydroxy-9H-xanthen-9-one and 2-adamantanone The dioxetane is thermally stable with an activation energy of 30.7 kcal/mol and a half-life at 25° C. of 12 years. The dioxetane is not only stable in organic solvents but also shows very slow spontaneous decomposition in aqueous buffers.

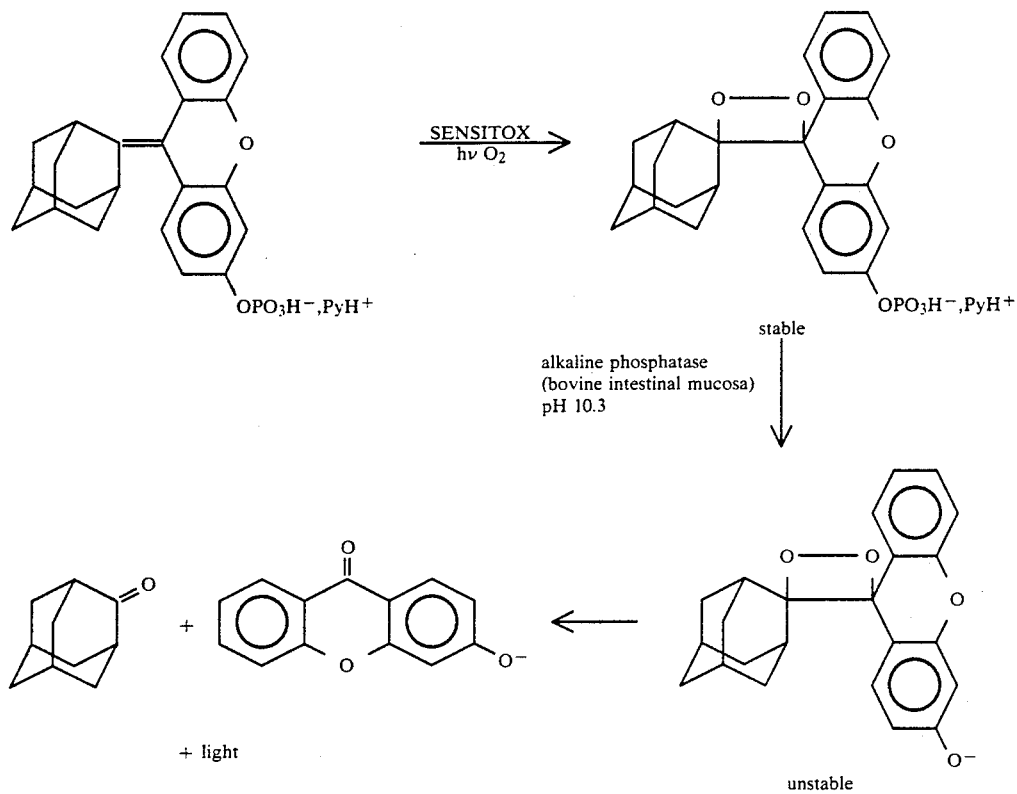

Triggering experiments were conducted using alkaline phosphatase from bovine intestinal mucosa [suspension of 5.3 mg of protein (1100 units/mg protein) per mL in 3.2 M $(NH_4)_2SO_4$] and the phosphate-protected dioxetane at pH 10.3 in 0.75 M 2-amino-2-methyl- 1-propanol buffer. A 50 μL aliquot (0.013 μmol) of a phosphate-dioxetane stock solution was added to 3 mL of the buffer at 37° C. to give a final dioxetane concentration of $4.2 \times 10^{-6}$M. Injection of 1 μL (final conc of protein=1.8 μg/mL) of alkaline phosphatase to the solution resulted in burst of chemiluminescence that decayed over a period of 3 min. Over this period of time, the background luminescence from slow non-enzymatic hydrolysis of the dioxetane in the buffer was only 0.2% of that produced by the enzymatic process The total light emission was found to be linearly dependent on the dioxetane concentration. The rate of decay of the emission is a function of enzyme concentration while the total light emission is independent of the enzyme concentration because of turnover of the enzyme. The chemiluminescence spectrum for the phosphatase-catalyzed decomposition was obtained at room temperature in the buffer solution A comparison of this chemiluminescence spectrum with the fluorescence spectrum of the spent reaction mixture and the fluorescence spectrum of the hydroxyxanthanone cleavage product in the buffer indicates that the emission is initiated by the enzymatic cleavage of the phosphate group in dioxetane to yield the unstable aryloxide dioxetane which generates the singlet excited anion of hydroxyxanthanone.

SPECIFIC DESCRIPTION

Synthesis of 1,2-Dioxetane Compounds and Fluorescent Surfactants

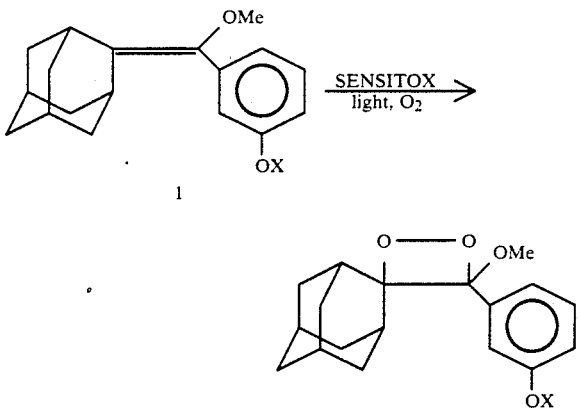

(a) X = H
(b) X = Ac
(c) X = $PO_3Na_2$

Instrumentation

Nuclear magnetic-resonance (NMR) spectra were obtained on either a Nicolet NT300 ™ or a General Electric QE300 ™ spectrometer as solutions in $CDCl_3$ with tetramethylsilane as internal standard unless noted otherwise. Infrared (IR) spectra were obtained on either a Nicolet ™ or a Beckman Acculab 8 ™ spectrometer. Mass spectra were obtained on either a Kratos ™ or an AEI MS-90 ™ spectrometer. Ultraviolet and visible absorption spectra were obtained on a Varian Cary 219 ™ spectophotometer. Fluorescence spectra were recorded on a Spex Fluorolog ™ spectrophotofluorometer. Chemiluminescence spectra were measured using the Spex Fluorometer. Chemiluminescence kinetic and quantum yield measurements were made with luminometers constructed in this laboratory. The instruments which use RCA A-31034A gallium-arsenide photomultiplier tubes cooled to −78° C. and Ortec photon-counting electronics are interfaced to Apple IIe ™ and Macintosh ™ computers. Elemental analyses were performed by Midwest Microlabs, Indianapolis. Melting points were measured in a Thomas Hoover ™ capillary melting apparatus and are uncorrected. Precision weights were obtained on a Cahn model 4700/ ™ electrobalance.

Materials o-Xylene was obtained from Burdick and Jackson Laboratories and used as received for kinetic and spectroscopic measurements. Dry DMF and DMSO were obtained by vacuum distillation from calcium hyride. Deuterium oxide, 1,4-dioxade-d$_8$, chloroform-d, fluorescein amine (isomer 1), and other chemical reagents were purchased from Aldrich Chemical Co. Samples of alkaline phosphatase were purchased from Sigma Chemical Co. SiLica, alumina and the other solid supports were obtained from various commercial sources and used without further purification.

Syntheses of Alkenes

[(3-Hydroxyphenyl)methoxymethylene]adamantane (1a). A 500-mL flask was fitted with a reflux condenser, a 125-mL addition funnel, and nitrogen line. The apparatus was dried by means of a hot air gun and nitrogen purging. Dry THF (40 mL) was added and the flask cooled in an ice bath. TiCl$_3$ (1.5 g, 10 mmol) was added rapidly followed by LAH (0.19 g, 5 mmol) in portions with stirring. The cooling bath was removed and the black mixture was allowed to warm to room temperature. Triethylamine (0.7 mL, 5 mmol) was added to the stirred suspension and refluxed for 15 minutes. After this period, a solution of methyl 3-hydroxybenzoate (152 mg, 1 mmol) and 2-adamantanone (300 mg, 2 mmol) in 20 mL of dry THF was added dropwise to the refluxing mixture over 15 minutes. Refluxing was continued for an additional 15 minutes after which the reaction was cooled to room temperature and diluted with 100 mL of distilled water. The aqueous solution was extracted with 3 ×50 mL portions of ethyl acetate. The combined organic layer was washed with water, dried over MgSO$_4$, and concentrated. Chromatography over silica with 15% ethyl acetate/hexane gave 240 mg (89%) of 1a as a white solid: mp 133°-4° C.; $^1$H NMR (CDCl$_3$)δ1.64–1.96 (m, 12H), 2.65 (s, 1H), 3.24 (s, 1H), 3.32 (s, 3H), 5.25 (s, 1H, OH exchange with D$_2$O), 6.70–7.30 (m, 4H), $^{13}$C NMR (CDCl$_3$)δ28.45, 30.36, 32.36, 37.30, 39.18, 39.33, 57.82, 114.60, 116.16, 122.19, 129.24, 137.24, 155.62; MS m/e (rel intensity) 271 (20, M+1), 270 (100, M), 253 (7.3), 213 (35.1), 121 (41.7), 93 (9.4); Exact mass: calcd 270.1619, found 270.1616.

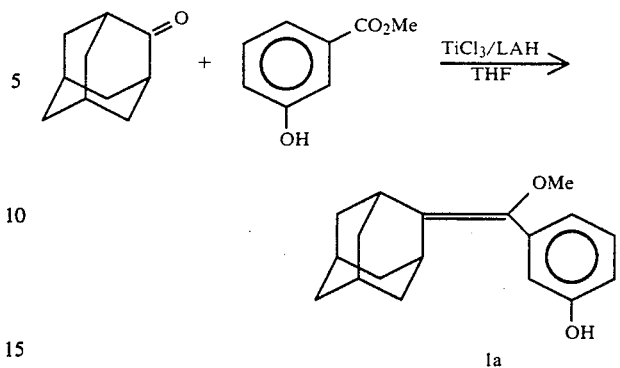

[(3-cetoxyphenyl)methoxymethylene]adamantane (1b). Hydroxy alkene 1a (0.75g, 2.8 mmol) was dissolved in 10 mL of CH$_2$Cl$_2$ and pyridine (5.2 g, 65.8 mmol) under N$_2$. The solution was cooled in an ice bath and a solution of acetyl chloride (2.6 g, 33 mmol) in 1 mL of CH$_2$Cl$_2$ was added dropwise via syringe. After 5 minutes at 0° C., TLC on silica with 20% ethyl acetate/hexane showed complete acetylation of 1a. After removal of the solvent, the solid residue was washed with 30 mL of ether. The ether was washed with 3×25 mL of water, dried over MgSO$_4$, and evaporated to dryness. The product was chromatographed on silica using 20% ethyl acetate/hexane affording 0 45g of 1b as an oil: $^1$H NMR (CDCl$_3$)δ1.79–1.96 (m, 12H), 2.27 (s, 3H), 2.66 (s, 1H), 3.26 (s, 1H), 3.29 (s, 3H), 6.99–7.36 (m, 4H); $^{13}$C NMR (CDCl$_3$) δ20.90, 28.13, 30.07, 31.99, 36.99, 38.89, 39.01, 57.59, 120.34, 122.14, 126.55, 128.66, 132.19, 136.90, 142.59, 150.42, 169.04; MS m/e (rel intensity) 312 (100, M), 270 (25), 255 (19.3), 213 (20.7), 163 (12.2), 121 (30.7), 43 (30); IR (neat) 3006, 2925 2856, 1725, 1600, 1438, 1362, 1218, 1100 cm$^{-1}$; Anal. Calcd. for C$_{20}$H$_{24}$O$_3$: C, 76.92; H, 7.69, Found: C, 76.96; H, 7.85.

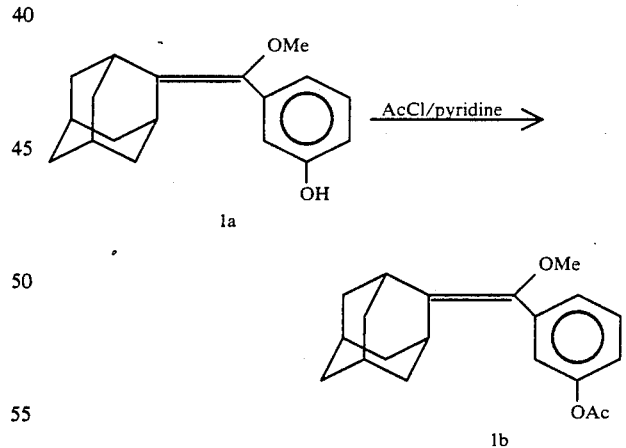

[(3-Phosphatephenyl)methoxymethylene]adamantane, disodium salt (1c).

Hydroxy alkene 1a (500 mg, 1.58 mmol) was dissolved in 5 mL of dry pyridine (dried over basic alumina). This solution was slowly added to a cold mixture of 1 mL (10.7 mmol) of phosphoryl chloride and 5 mL of dry pyridine at such a rate that the temperature of the reaction remained below 5° C. After 30 minutes the reaction was terminated and the phosphoryl dichloridate product was poured onto a mixture of 20 g of ice and 1 mL of 10 N sodium hydroxide. The mixture was transferred to a separatory funnel and washed with 5×30 mL portions of CH$_2$Cl$_2$. The product precipitated from the aqueous fraction after overnight refrigeration. The solid material was washed with 3×10 mL portions of CH$_2$Cl$_2$ followed by 3×10 ML portions of cold water. The white solid was then dried under reduced pressure to give 400 mg (1.02 mmol, 64%) of phosphorylated alkene 1c: $^1$H NMR (D$_2$O/p-dioxane-d$_8$) δ 1.67–1.83 (m, 12H), 2.50 (s, 1H) 3.04 (s, 1H) 3.19 (s, 3H) 6.7–7.2 (m 4H) $^{13}$C NMR (D$_2$O) δ 28.29, 30.44, 32.45, 36.99, 38.89, 57.98, 120.16, 120.85, 123.74, 128.89, 133.15, 136.11, 142.68, 154.45; $^{31}$P NMR (D$_2$O/p-dioxane-d$_8$) δ1.586.

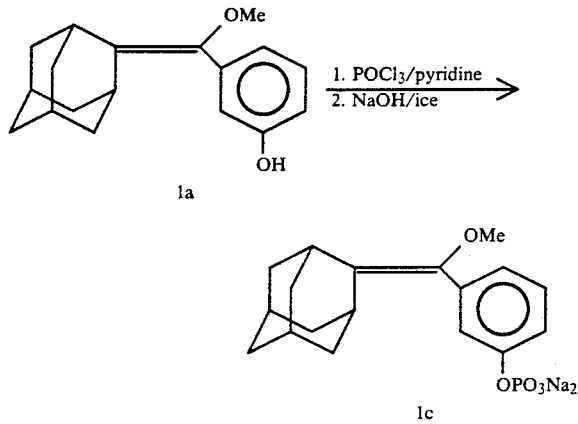

Synthesis of fluorescein Surfactant 5-(N-tetradecanoylaminofluorescein (3)

A solution of myristoryl chloride (2.18 g, 8.83 mmol) in THF was added to a solution of fluoresceinamine-isomer 1 from Aldrich Chemical Co. (3.07 g, 8.85 mmol) in dry pyridine (dried over basic alumina) dropwise with stirring at room temperature over a 12 hour period. TLC on silica with 20% MeOH/benzene showed conversion to a less polar product. The reaction was poured into ice water and the solid precipitate isolated by filtration to give 4 g of solid orange material Column chromatography with 10% MeOH/benzene afforded 500 mg of the pure product as an orange solid: mp 185–190° C.; $^1$H NMR (CDCl$_3$)δ 0.88 (t, 3H), 1.27 (m, 20H), 1.74 (m, 2H), 2.42 (t, 2H), 6.54–8.32 (m, 9H); $^{13}$C NMR (CDCl$_3$) δ 13.05, 22.27, 25.34, 28.90, 29.01, 29.17, 29.31, 31.61, 36.65, 101.00, 110.25, 112.43, 114.93, 124.41, 126.58, 127.86, 128.77, 140.41, 147.00, 152.89, 160.28, 169.96, 173.65; MS (FAB) m/e (rel intensity) 558 (10, M+1), 402 (14.7), 388 (14.2), 374 (12.5), 348 (28.1), 302 (35.2), 213 (36.4), 165 (36.4), 133 (50). The properties of 3 are in agreement with those described for the commercially available material from Molecular Probes, Inc.

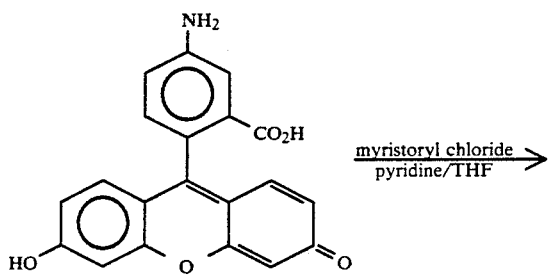

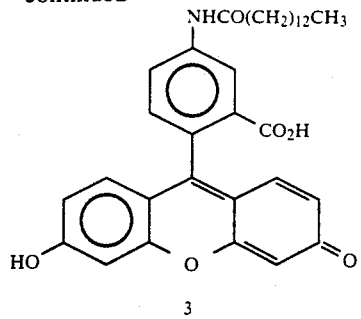

3

Synthesis of 1-Hexadecyl-6-hydroxy-2-benzothiazamide (4)

Methyl 6-hydroxy-2-benzothiazoate (60 mg, 0.30 mmol) [see F. McCapra and Z. Razani, *Chem. Commun.*, 153 (1976)] and 1-hexadecylamine (430 mg, 1.8 mmol) were dissolved in methanol. After refluxing the solution for two days, thin layer chromatography with 40% EtOAc/hexane showed conversion of the benzothiazoate to a less polar material. The methanol was evaporated and the residue was then chromatographed with 2% EtOAC/hexane to remove the excess 1-hexadecylamine. The chromatography was then continued with 50% EtOAC/hexane and afforded 4 as a white solid: 33 mg (27%); mp 82–4° C.; $^1$H NMR (acetone-d$_6$) δ 0.83 (t, 3H), 1.32 (br 26H), 1.66 (m, 2H), 3.43 (t, 2H), 7.10–7.88 (m, 3H), 8.15 (br. 1H, OH exchanges with D$_2$O); $^{13}$C NMR (benzene-d$_6$) δ 14.29, 23.05, 27.08, 29.58, 29.66, 29.75 29.86, 30.13, 32.28, 39.98, (acetone-d$_6$) δ 107.51, 117.69, 125.61, 139.33, 147.80, 157 63, 160.4(, 162.12; MS (m/e (rel. intensity) 418 (M+, 33.7), 360 (14.1), 240 (61.1), 178 (77.3), 151 (39.1), 97 (28.6), 83 (34.7); Exact mass: calcd. 418.2653, found 418.2659 for C$_{24}$H$_{38}$N$_2$O$_2$S.

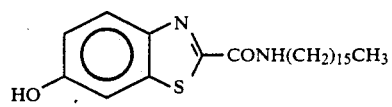

4

Preparation of 1,2-Dioxetanes

Photooxygenation procedure. Typically a 5–10 mg sample of the alkene was dissolved in 5 mL of CH$_2$Cl$_2$ in the photooxygenation tube. Approximately 40 mg of polystyrene-bound Rose Bengal (Sensitox I) [reference to this type of sensitizer: A. P. Schaap, A. L. Thayer, E. C. Blossey, and D. C. Neckers, *J. Amer. Chem. Soc.*, 97, 3741 (1975)] was added and an oxygen bubbler connected. Oxygen was passed slowly through the solution for 5 minutes and the apparatus immersed in a half-silvered Dewar flask containing dry ice/2-propanol. The sample was irradiated with either a 250 W or 1000 W sodium Lamp (General Electric Lucalox) and a UV cutoff filter while oxygen was bubbled continuously. Progress of the reaction was monitored by TLC. A spot for the highly stable dioxetanes could usually be detected and had a R$_f$slightly less than that of the alkene. The adamantyl-substituted dioxetanes were filtered at room temperature, evaporated on a rotary evaporator and recrystallized from a suitable solvent.

4-(3-Hydroxyphenyl)-4-methoxyspiro[1,2-dioxetane-3,2'-adamantane](2a).

Hydroxy alkene la (100 mg) was irradiated with the 1000W Na lamp in 8 mL of $CH_2Cl_2$ at $-78°$ C. in the presence of Sensitox I. The alkene and dioxetane on TLC using 20% ethyl acetate/hexane exhibit the same $R_f$ value. Therefore, the reaction was stopped w[en a trace of the cleavage product began to appear. The sensitizer was removed by filtration and the solvent evaporated. lH NMR was used to check that all of the starting material had been oxidized Dioxetane 2a was recrystallized from pentane/benzene to give a white solid: mp 135° C.: lH NMR ($CDCl_3$) $\delta$ 1.04–2.10 (m, 12H), 2.21 (s, lH), 3.04 (s, lH), 3.24 (s, 3H), 6.48 (s, lH, OH exchange with $D_2O$), 6.93 7.30 (m, 4H). 13C NMR ($CDCl_3$) $\delta$ 25.81, 25.95, 31.47, 31.57, 32.27, 32.86, 33.07, 34.58, 36.30, 49.83, 95.88, 112.08, 116.46, 129.34, 136.1, 156.21.

4-(3-Acetoxyphenyl)-4-methoxyspiro[1,2-dioxetane-3,2'-adamantanel(2b). Alkene lb (140 mg, 0.45 mmol) was photooxygenated in 30 mL of $CH_2Cl_2$ at $-78°$ C. with the 1000 W high pressure sodium lamp using 400 mg of Sensitox I. TLC analysis on silica gel with 20% ethyl acetate/hexane showed clean conversion to a more polar material in 2.5 h. NMR ($CDCl_3$) $\delta$ 0.90–1.90 (m, 12H), 2.15 (s, lH), 2.31 (s, 3H), 3.03 (s, lH), 3.23 (s, 3H), 6.61–7.45 (m, 4H) $^{13}$C NMR ($CDCl_3$) $\delta$ 21.00, 25.82, 25.97, 31.50, 31.65, 32.21, 32.80, 33.09, 34.71, 36.32, 49.92, 95.34, 111.50, 122.58, 129.16, 136.42, 150.72, 169.11.

4-Methoxy-4-(3-phosphatephenyl)spiro[1,2-dioxetane-3,2'-adamantane], disodium salt (2c) Alkene lc (50mg) was photooxygenated in 2 mL of $D_2O$/p-dioxane-$d_8$ (1:1 v/v) at 10° C. with the 1000 W high pressure sodium lamp using Sensitox I. $^1$H NMR analysis showed clean conversion to dioxetane 2c in 45 minutes. The sensitizer was removed by filtration and the filtrate used as a stock solution for chemiluminescence experiments. $^1$H NMR ($D_2O$/p-dioxane-$d_8$ $\delta$ 0.91–1.70 (m, 12H), 2.08 (s, lH), 2.80 (s, lH) 3.07 (s, 3H), 7.00–7.26 (m, 4H); $^{13}$C NMR ($D_2O$/p-dioxane-$d_8$) $\delta$ 28.95, 30.95, 32.98, 37.65, 39.53, 58.31, 120.62, 121.64, 123.55, 129.31, 132.45, 136.57, 143.98, 155.30.

Chemiluminescence Kinetics Procedures

Rates for thermal decomposition of the stable dioxetanes were monitored by the decay of chemiluminescence of aerated solutions. A cylindrical Pyrex vial equipped with magnetic stir bar was filled with 3–4 mL of the reaction solvent, sealed with a Teflon-lined screw cap and placed in the thermostatted sample block of the chemiluminescence-measuring luminometer. Temperature control was provided by an external circulating water bath. Appropriate values for the instrument gain and optical slit size were selected. When thermal equilibrium was reached (ca. 3 minutes), an aliquot of the dioxetane stock solution sufficient to achieve a final concentration not greater than $10^{-4}$ M was added via pipette by opening the top of the luminometer or via syringe through a light-tight rubber septum located in the cover directly above the vial. The vial was sealed with a Teflon-lined screw cap to prevent evaporation when high temperatures were used. Measurement of the signal was begun by opening the shutter. The chemiluminescent decay was generally recorded for at least three half-lives. Calculation of the first-order rate constant (k) from the In (Intensity) vs. time data was performed by a computer program utilizing a standard least-squares treatment. The correlation coefficient (r) was typically at least 0.999 and k varied less than 5% between replicate samples.

Figure 1:
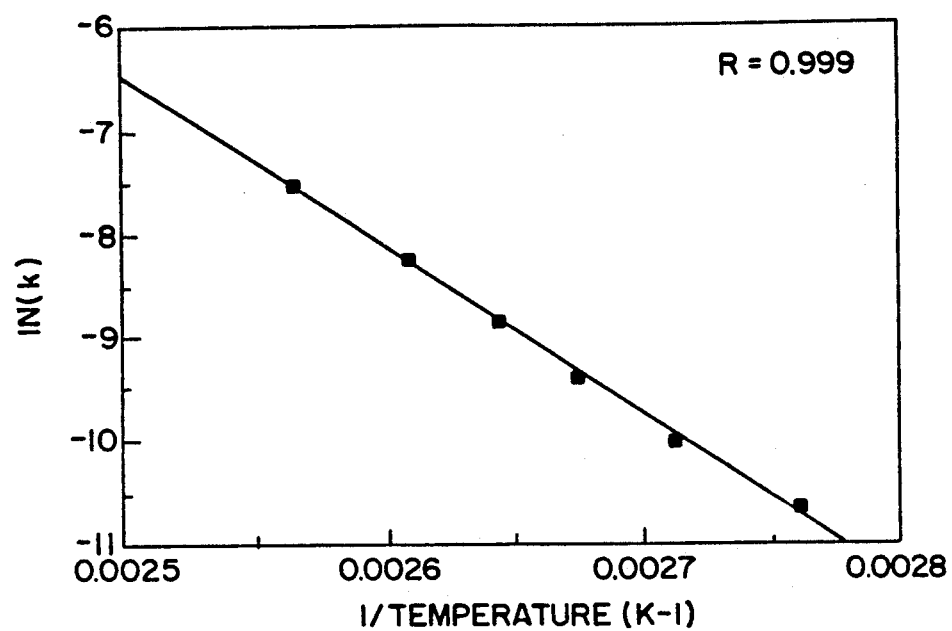
FIG. 1 shows Arrhenius plot for the thermal decomposition of phosphate-substituted dioxetane 2c in xylene.

Activation parameters for decomposition of the dioxetanes were calculated from plots of In k vs. 1/T (Arrhenius eq.) or In k/t vs. 1/T (Eyring eq.) by a standard least-squares linear regression analysis. The results of replicate runs at 5 to 10 temperatures encompassing a temperature range of 80° to 120° C. were found to yield a straight line with a correlation coefficient of 0.99 or better. For example, FIG. 1 shows an Arrhenius plot for the thermal decomposition of phosphate-substituted dioxetane 2 c in o-xylene with $E_a=32.5$ kcal/mol and r=0.999. The half-life for 2 c at 25° C. is calculated from the Arrhenius equation to be 19 years.

Activation Energies for Thermal Decomposition of Dioxetanes in Xylene.

| Dioxetane (X) | $E_a$ | Log A | k(sec$^{-1}$) at 25° C. | $t_{\frac{1}{2}}$ at 25° C. |
|---|---|---|---|---|
| 2a (OH) | 28.3 | 12.5 | $5.38 \times 10^{-9}$ | 4.1 yrs |
| 2b (OAc) | 30.4 | 13.6 | $1.73 \times 10^{-9}$ | 13 yrs |
| 2c ($PO_3Na_2$) | 32.5 | 14.9 | $1.19 \times 10^{-9}$ | 19 yrs |

The above results demonstrate the extremely high stability (long half-life) that these types of dioxetanes exhibit before triggering with the appropriate chemical agent or enzyme.

Determination of Chemiluminescence Quantum Yields

The chemiluminescence quantum yield ($\Phi_{CL}$) for the decomposition of dioxetanes is defined as the ratio of einsteins of chemiluminescence emitted to moles of dioxetane decomposed. Sufficient energy is released during the reaction from the reaction enthalpy ($\Delta H_R$) plus the Arrhenius activation energy ($E_a$) to populate the singlet excited state of one of the carbonyl cleavage products. Therefore, the maximum quantum yield is 1.0. Another parameter of interest is the chemiexcitation quantum yield ($\Phi_{CE}$) which is defined as the ratio of excited states formed to dioxetane decomposed. The chemiexcitation quantum yield is related to the chemiluminescence quantum yield via the fluorescence quantum yield of the dioxetane cleavage ($\Phi_F$) through the equation: $\Phi_{CL}=\Phi_{CE} \times \Phi_F$.

The same procedure as those employed in the measurement of the decay kinetics was used for the determination of chemiluminescence quantum yields with the following modifications. An accurately measured aliquot of a dioxetane stock solution of known concentration was added to 3 mL of the pre-thermostatted organic solvent or aqueous buffer. The reaction was then triggered by adding the appropriate chemical reagent or enzyme. The total light intensity was integrated by a photon-counting luminometer using an RCA A-31034A gallium-arsenide PMT cooled to $-78°$ C. Light intensity was converted to photons by reference to a calibration factor based on the accurately known quantum yield of the chemiluminescent reaction of luminol with base in aerated DMSO. The luminol reaction has been determined to have a chemiluminescence quantum yield of 0.011 (1.1%) (J. Lee and H. H. Seliger, *Photochem. Photobiol.*, 15, 227 (1972); P. R. Michael and L. R. Faulkner, *Anal. Chem.*, 48, 1188 (1976)).

Acquisition of Chemiluminescence Spectra

Spectra of the chemiluminescence from chemically or enzymatically triggered dioxetanes were obtained by conducting the reaction in a 1-cm square quartz cuvette in the sample compartment of a Spex Fluorolog spectrofluorometer at ambient temperature. Correction for the decay of the chemiluminescence intensity during the wavelength scan was made by accumulating the spectrum in a ratio mode so that the observed spectrum was divided by the signal from an auxiliary detector (EMI 9781B) which measures the total signal as a function of time. The monochromator bandpass was typically 18 nm. For weakly emitting samples, several identical scans were performed and added together to improve the signal-to-noise ratio.

Chemical Triggering of Dioxetanes

1. Triggering the Chemiluminescence of Hydroxy-Substituted Dioxetane 2a with Base. Treatment of $10^{-4}$ M solution of dioxetane 2a in DMSO at room temperature with an excess of tetra-n-butylammonium hydroxide resulted in intense blue chemiluminescence which decayed over a period of several minutes. The emission maximum for the chemiluminescence is 470 nm. The fluorescence of the anion of the cleavage product (methyl 3-hydroxybenzoate, MHB) is identical to the chemiluminescence spectrum. These results demonstrate that the chemiluminescence process involves: (a) base triggering to yield the unstable aryloxide form of the dioxetane, (b) subsequent cleavage of this species to generate MHB in the singlet excited state, and (c) fluorescence of MHB to yield the luminescence with an overall quantum yield ($\Phi_{Cl}$) of 0.25.

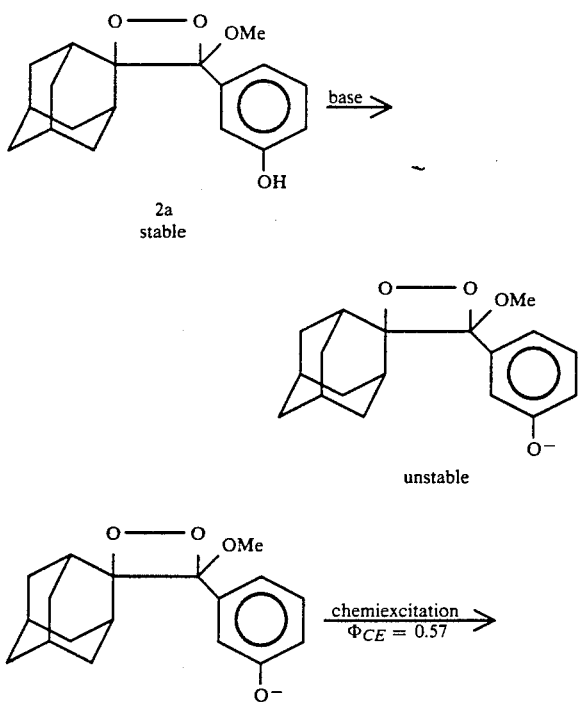

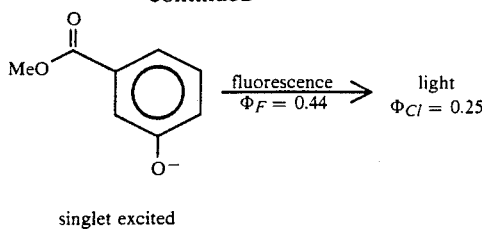

2. Catalysis of the Base-Triggered Chemiluminescence of Acetoxy-Substituted Dioxetane 2b in Aqueous Micelles: Enhanced Chemiluminescence Efficiency via Intermolecular Energy Transfer. Cationic surfactants such as cetyltrimethylammonium bromide (CTAB) can be used to increase rates for chemical triggering of chemiluminescence from appropriately substituted dioxetanes in aqueous solution. For example, CTAB catalyzes the base-induced luminescent cleavage of the acetoxy-substituted dioxetane 2b. The dioxetane is solubilized in the micelles formed by the surfactant and NaOH is added to initiate the chemiluminescence. The electrostatic attraction of the cationic head group and the hydroxide anion provides the observed micellar catalysis. Typically, the experiments were carried out with $[2b]=9.1 \times 10^{-5}$ M, $[CTAB]=2\times10^{-3}$ M, and $[OH^-]=9.1\times10^{-5}$ M at 37° C.

Figure 2:
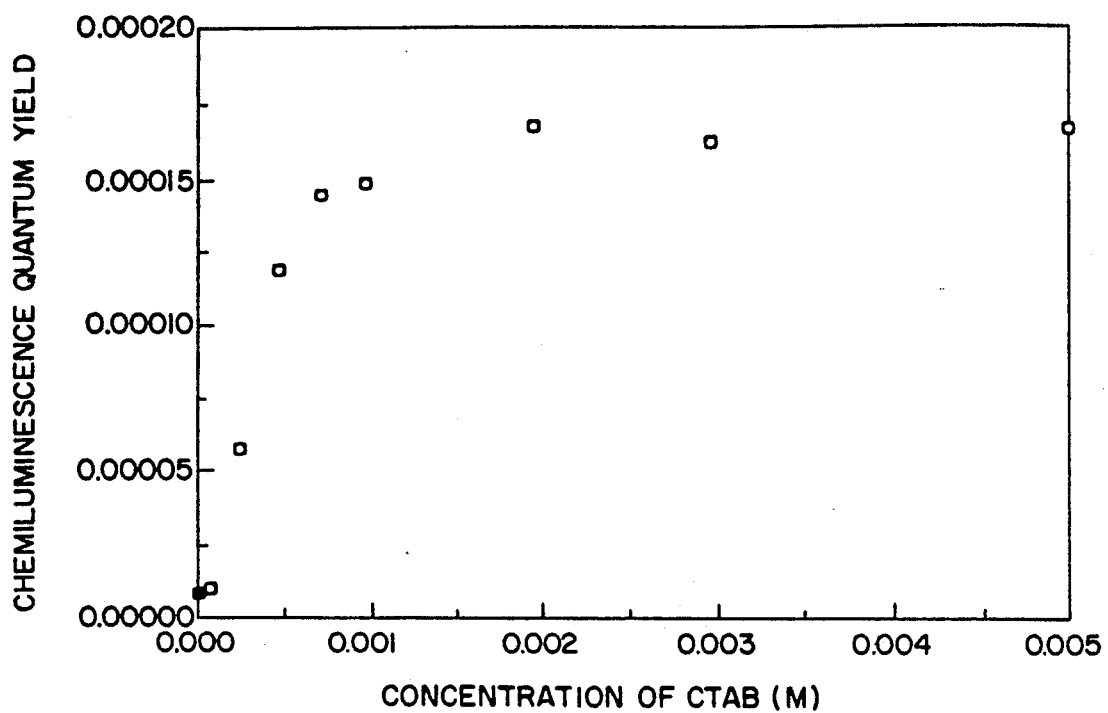
FIG. 2 shows a plot of chemiluminescence quantum yield for base-triggered reaction of dioxetane 2b as a function of the concentration of cetyltrimethylammonium bromide (CTAB).

The micellar environment can lead to higher chemiluminescence efficiencies. Although the light yields of 2a and 2b with base in DMSO are extremely high at 0.25, the yield for these dioxetanes in water is only $8.9\times10^{-6}$. The principal reason for this large decrease results from the fact that the cleavage product (MHB) is only weakly fluorescent in water However, as demonstrated by the following experiment, the luminescence can be enhanced by triggering the dioxetane in a micelle. The conditions for base-triggering of 2b were the same as described above except that the concentration of CTAB was varied from 0 to $5\times10^{-3}$ M. FIG. 2 shows a 19-fold increase in the chemiluminescence quantum yield ($\Phi_{Cl}=1.7\times10^{-4}$) above the critical micelle concentration for CTAB (cmc≅$1\times10^{-3}$ M). Enhanced chemiluminescence efficiency in the micellar environment is the result of increases in $\Phi_F$ and/or $\Phi_{CE}$.

Figure 2A:
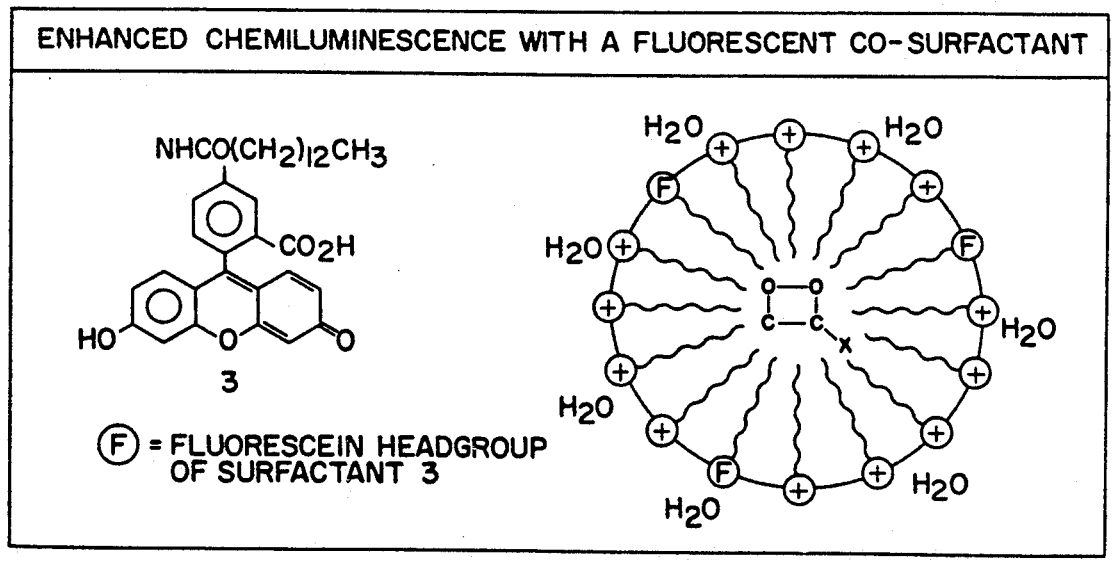
FIG. 2a shows an idealized structure of a dioxetane with a fluorescent co-surfactant and CTAB surfactant.

Incorporation in the micelle of a co-surfactant with a fluorescent head group provides dramatically higher chemiluminescence yields for both chemically and enzymatically triggered dioxetanes energy transfer from the excited cleavage product to the fluorescent surfactant can be very efficient because both the triggerable dioxetane and the energy acceptor (fluorescer) are held in close proximity in the micelle as illustrated in FIG. 2a.

For example, CTAB micelles containing fluorescein surfactant 3 and dioxetane 2b were prepared in aqueous solution with final concentrations of: CTAB ($1.5\times10^{-3}$ M), 3 ($9\times10^{-5}$ M), and 2b ($9\times10^{-5}$ M). Addition of base at 37° C. resulted in intense yellow chemiluminescence rather than the normal blue emission with a chemiluminescence efficiency of 1.4% ($\Phi_{CL}=0.014$), an increase of 500-fold over the luminescence of 2b in the absence of CTAB and 3.

Similar experiments were conducted with the benzothiazamide surfactant 4. The chemiluminescence efficiency was 0 3% with $\lambda_{max}$ at 506 nm.

Enzymatic Triggerinq of Phosphate-Substituted Dioxet 2c.

Figure 3:
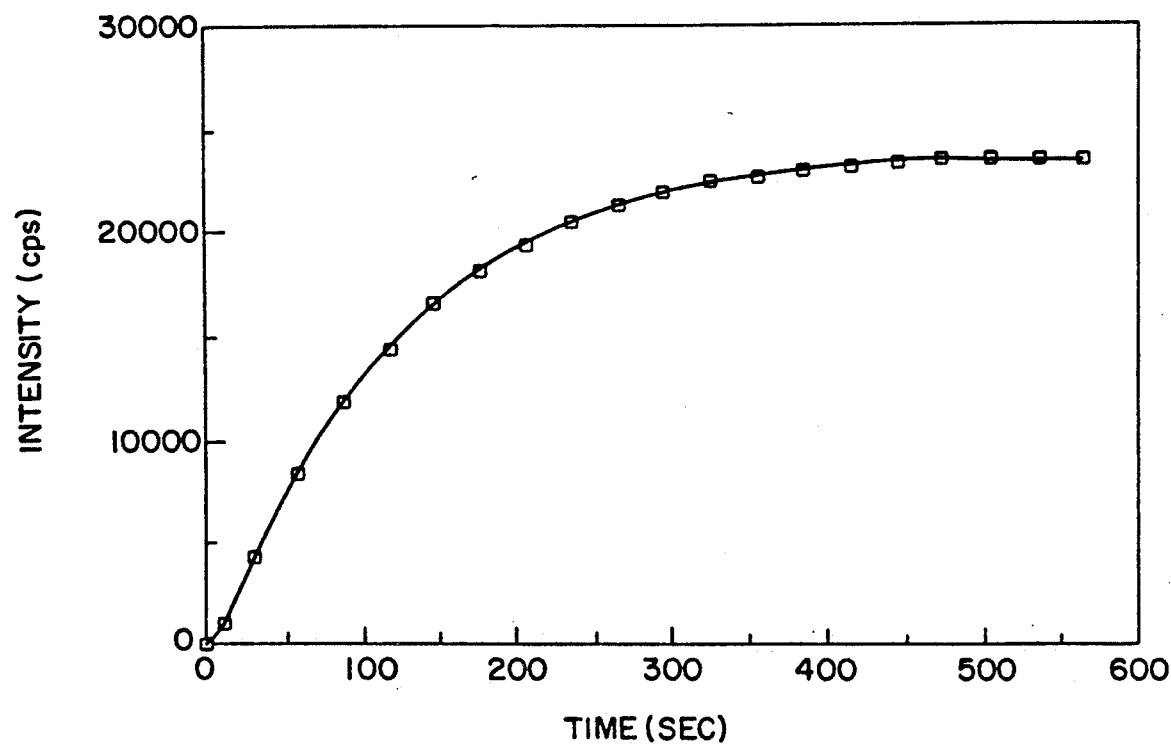
FIG. 3 shows a plot of chemiluminescence intensity vs. time for $10^{-5}$ M dioxetane 2c with 100 microliters of human blood serum containing alkaline phosphatase in 2-amino-2-methyl-1-propanol (221) buffer (pH 10.3) at 37° C.
Figure 4:
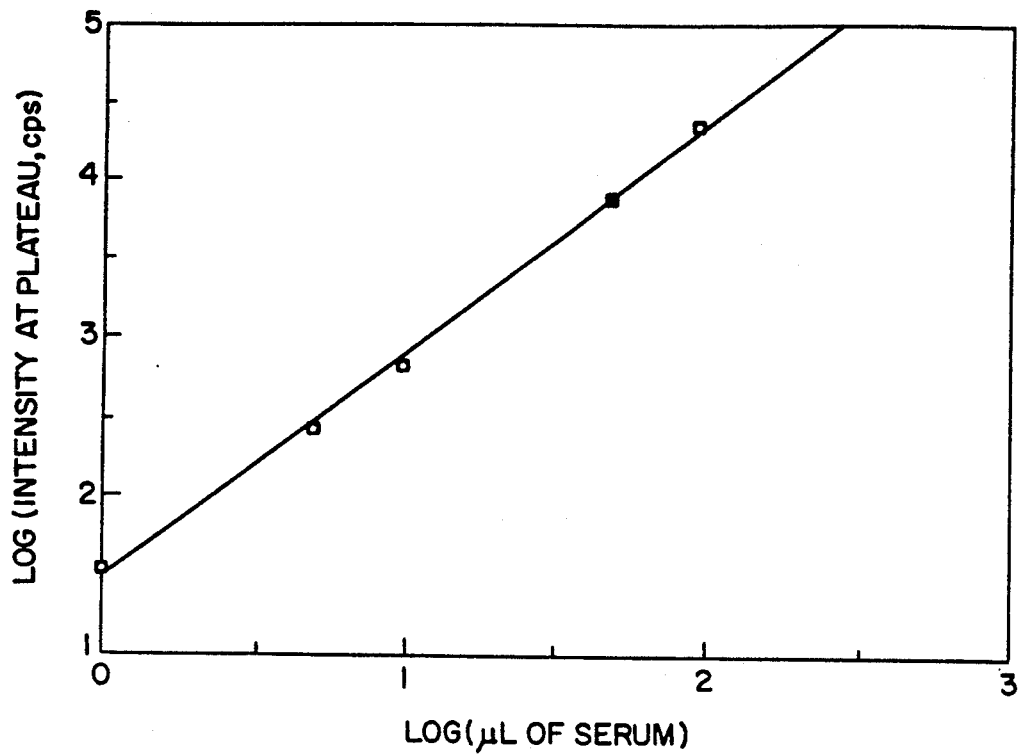
FIG. 4 shows a plot of log (light intensity at plateau) vs. log (microliters of serum, 1-100) for dioxetane 2c.
Figure 5:
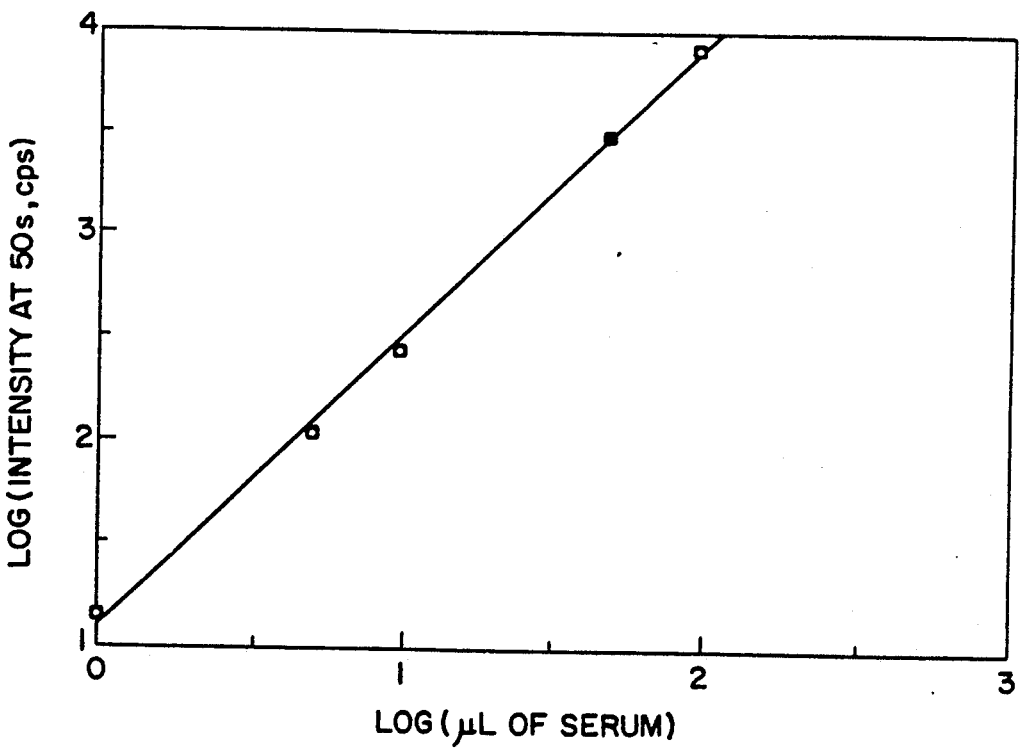
FIG. 5 shows a plot of log (light intensity at 50 sec) vs. log (microliters of serum, 1-100) for dioxetane 2c.

1. Triggering the Chemiluminescence of 2c with Alkaline Phosphatase from Human Blood Serum. A stock solution of dioxetane 2c was prepared in dioxane/water (1:1 v/v) by photooxygenation of 1c. A sample of fresh blood was drawn from a healthy donor and the red blood cells removed by centrifugation to provide serum for the experiments. Treatment of 3 mL of a $10^{-5}$ M solution of 2c in 0.75 M 2-amino-2-methyl-1-propanol (221) buffer (pH 10.3) at 37° C. with 100 µL of serum led to the typical intensity vs. time profile shown in FIG. 3 where the serum is injected at time zero. Under these conditions the light intensity reaches a constant level of approximately $2.3 \times 10^4$ counts/sec. The background luminescence signal from non-enzymatic hydrolysis of 2c is less than 0.05% of the enzyme-generated value. The light intensity at the plateau is directly proportional to the enzyme concentration as shown by a series of experiments using 100 to 1 µL of serum (FIG. 4) The light intensity at any other time point can also be conveniently used to provide a direct measure of the enzyme concentration (FIG. 5).

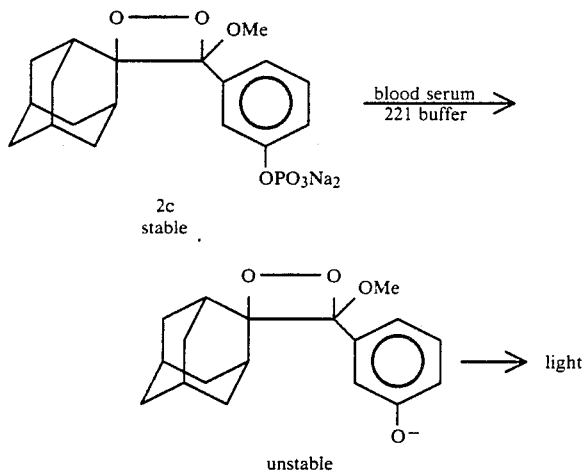

2. Triggering the Chemiluminescence of 2c with Alkaline Phosphatase from Bovine Intestinal Mucosa. Alkaline phosphatase from bovine intestinal mucosa was obtained from Sigma Chemical Co. as a suspension of 5.1 mg of protein per mL of 3.2 M $(NH_4)_2 SO_4$ solution. In a typical experiment, 50 µL of a $2.56 \times 10^{-3}$ M stock solution of dioxetane 2c in 221 buffer was added to 3 mL of 221 buffer (0.75 M, pH 9.1) containing $8.0 \times 10^{-4}$ M $Mg(OAc)_2$ giving a final dioxetane concentration of $4.3 \times 10^{-5}$ M. Injection of a 10 µL aliquot of diluted enzyme into the solution at 37° C. resulted in chemiluminescence, the quantum yield of which was $3.1 \times 10^{-5}$. As with chemical triggering, the addition of CTAB ($1.13 \times 10^{-3}$) results in a modest increase in $\Phi_{Cl}$ to $2.1 \times 10^{-4}$. The kinetics of the enzymatic triggering were not significantly altered by the presence of the surfactant.

3. Triggering the Chemiluminescence of 2c with Alkaline Phosphatase: Enhanced Chemiluminescence Efficiency via Intermolecular Energy Transfer il Aqueous Micelles. The efficiency of the enzyme triggered chemiluminescence of 2c can be dramatically enhanced by incorporation of the fluorescein co-surfactant 3 in the micelles. Alkaline phosphatase experiments with dioxetane 2c were conducted at 37° C. with 3 mL of a solution containing: 2c ($4.3 \times 10^{-5}$ M), 221 buffer (0.75 M, pH 9.1), $Mg(OAc)_2$ ($8.0 \times 10^{-4}$ M), CTAB ($1.13 \times 10^{-3}$ M), and fluorescein surfactant 3 ($5.6 \times 10^{-5}$ M). Addition of alkaline phosphatase (Sigma, bovine intestinal mucosa) to give a final concentration of 12 pg/mL of protein resulted in chemiluminescence over a 45 minute period Integration of the light intensity over the entire course of light emission gave $\Phi_{Cl} = 0.015$ (or 1.5% chemiluminescence efficiency, a 500-fold increase compared to the enzymatic reaction in the absence of CTAB and 3). As in the case of chemical triggering of 2b, the chemiluminescence spectrum is also stifted from the normal blue emission (FIG. 6, Curve A) to the typical fluorescein emission (FIG. 6, Curve B), demonstrating the involvement of energy-transfer processes. It should be emphasized that simple reabsorption cf the blue light by 3 and subsequent fluorescence cannot be the mechanism for the spectral shift as such a process would not result in enhanced efficiency.

To test the sensitivity of this chemiluminescence method for evaluating concentrations of alkaline phosphatase in solution, a series of experiments were carried out using enzyme stock solutions prepared by dilutions of the commercial sample obtained from Sigma. A conservative estimate of the concentration of phosphatase in the sample was made by assuming that the 5.1 mg of protein per mL in the sample was 100% pure alkaline phosphatase A molecular weight of 140,000 as also used in calculating molar amounts of enzyme. The conditions were the same as described above with 2c, CTAB, and fluorescer 3 except that the final quantities cf enzyme in the 3 mL solutions were:

A = $3.6 \times 10^{-12}$ moles
B = $3.3 \times 10^{-13}$ moles
C = $3.0 \times 10^{-14}$ moles
D = $2.7 \times 10^{-15}$ moles
E = $2.5 \times 10^{-16}$ moles
F = $2.3 \times 10^{-17}$ moles Under these conditions the background chemiluminescence from the non enzymatic hydrolysis of 2c in the buffer/co-micelle environment is extremely slow and gives rise to a constant signal of only a few counts/sec (FIG. 7). A typical intensity vs. time profile for enzymatic triggering with a phosphatase concentration of $2.7 \times 10^{-15}$ moles in 3 mL (Experiment D) is shown in FIG. 7. The light intensity increases with time over a period of 30-60 minutes depending on enzyme concentration. After this period the light remains constant until the dioxetane is consumed. The pre-steady state period can be eliminated if the sample containing the dioxetane and enzyme is incubated at 37°-45° C. for several minutes before analysis with the luminometer.

Plots of either the integrated light intensity or intensities at a specific time point vs. the quantity of enzyme give excellent correlations For example, FIG. 8 shows a plot of the log (total enzymatic luminescence from time zero to 3 minutes) vs. log (moles of alkaline phosphatase). The reproducibility of each run was better than 4% and plots such as shown in FIG. 8 gave correlation coefficients of >0.99.

Enzymatic triggering experiments such as those described above were also carried out in Immumlon ™ microtitre wells from Dynatech, Inc. made of transparent polystyrene. The wells were used individually and placed in a light-tight holder which could be thermostatted. The chemiluminescence was detected at the bottom of the well using a fiber optic connected to the photon-counting luminometer described previously. This experimental set-up allowed much smaller reaction volumes to be used. For example, a series of experiments using dioxetane 2c, CTAB, and 3 in 200 μL of 221 buffer with amounts of alkaline phosphatase ranging from $5 \times 10^{-15}$ to $2 \times 10^{-18}$ moles (or 2 attomoles) were carried out FIG. 9 shows the intensity vs. time profile for an experiment with $2.3 \times 10-17$ moles of enzyme. A more realistic assumption for the purity of the enzyme sample might be 10.% Under those conditions it is seen from FIG. 10 that this chemiluminescent technique with dioxetane 2c permits the detection of less than 0.2 attomoles of alkaline phosphatase.

The chemiluminescence generated by the enzymatic triggering of dioxetane 2c can also be detected photographically using X-ray film and instant film. For example FIGS. 11 and 12 show the chemiluminescence recorded on ASA 3000 Polaroid TM, Type 57 film. Solutions of 221 buffer (100 μL, 0.75 M, pH 9.1) containing dioxetane 2c $4.3 \times 10^{-5}$ M), Mg(OAc)$_2$ ($8.0 \times 10^{-4}$ M), CTAB ($1.13 \times 10^{-3}$ M), and fluorescein surfactant 3 ($5.6 \times 10^{-5}$ M) were incubated in Dynatech Immulon wells in the presence of varying amounts of alkaline phosphatase using the same enzyme stock solutions listed above. The wells were incubated for 1 hour at 37° C. and then photographed at that temperature for 15 minutes by placing the wells directly on the film in a light-tight incubator. The light intensity recorded on the film clearly provides a measure of the enzyme concentration.

4. Chemiluminescent Enzyme-Linked Assays. Enzymatic triggering of appropriately substituted dioxetanes provides an ultrasensitive detection method for enzyme-linked biological assays. For example, phosphate-substituted dioxetane 2c can be used with enzyme linked immunoassays and DNA probes that utilize alkaline phosphatase as the marker for detection. Previous detection methods make use of substrates which develop a color or become fluorescent upon reaction with this enzyme. The sensitivity of the chemiluminescent technique with dioxetane 2c is illustrated by an enzyme-linked immunosorbant assay (ELISA) for the retinal protein, S-antigen. Using procedures of L. A. Donoso (L. A. Donoso, C. F. Merryman, K. E. Edelberg, R. Naids, and C. Kalsow, *Investigative Ophthalmology & Visual Science* 26 561 (1985)), a series of 7 Immulon TM wells were coated with varying amounts of S-antigen (112, 56, 28, 14, 7, 3, 1.3 ng), reacted with a monoclonal antibody (MAbA9-C6) developed in mouse, and finally reacted with anti-mouse IgG coupled to alkaline phosphatase. A chemiluminescence assay of each well was then conducted individually by adding 100 μL of 221 buffer (0.75 M, pH 9.1) containing Mg(OAc)$_2$ ($8.0 \times 10^{-4}$ M), CTAB ($1.13 \times 10^{-3}$ M), and fluorescein surfactant 3 ($5.6 \times 10^{-5}$ M). The well was placed in the micro-luminometer and equilibrated to 37° C. for 3 minutes and 10 μL of a stock solution of dioxetane 2c in 221 buffer was injected to give a final concentration of 2c of 1 $36 \times 10^{-4}$ M. A typical chemiluminescence intensity vs. time profile is shown in FIG. 13. The reagent background luminescence is very low and constant at 15-20 counts/sec (FIG. 13). As shown in FIG. 14, The integrated light intensity correlates with the amount of antigen coated on the well. Following the experiments with the luminometer, the wells containing the same solution were subsequently used for a photographic detection experiment (FIG. 15). The 7 wells were placed in a holder and incubated for 30 minutes at 37° C. and then photographed at that temperature with ASA 3000 Polaroid TM Type 57 film for 15 min in a light-tight incubator. As shown in FIG. 15, the light intensity recorded on the film also correlates with the amount of S-antigen coated on the well. The reproducibility of the photographic assay is illustrated in FIG. 16. Four wells coated with 50 ng of antigen were treated with buffer and dioxetane as above, incubated for 1 hour at 45° C., and then photographed with the film for 30 sec at that temperature It should be noted that in both photographic assays the control well containing only buffer solution and dioxetane is not visible, again demonstrating the extremely low background produced by non-enzymatic hydrolysis of the dioxetane.

5. Enzymatic Triggering of Hydroxy-Substituted Dioxetane 2a with Urease in the Presence of Fluorescent Micelles. A solution was prepared using 160 mg of CTAB and 12.4 mg of fluorescein surfactant 3 in 200 mL of distilled water. A urea solution was made by dissolving 200 mg of urea in 100 mL of distilled water with EDTA added to give a final concentration of 0.4 mM. The substrate solution for the urease experiments was obtained by mixing 10mL of each stock solution.

Experiments were carried out with urease (Sigma) by incubation at room temperature for periods of 0.5 to 2 hours. Subsequent injection of 10 μL of $3 \times 10^{-3}$ M dioxetane 2a produced chemiluminescence which was monitored by the luminometer and by instant film. The intensity of the luminescence provided a measure of the concentration of urease.

In the preferred method and compositions, the dioxetane is used in an amount between about $10^{-2}$ and $10^{-6}$ M; the surfactant in an amount greater than about 10-4 M and the co-surfactant fluorescein surfactant in an amount between about $10^{-3}$ and $10^{-6}$ M. The co-surfactant quenches itself when used alone in solution In general the molar ratio of the dioxetane to fluorescent compound is between about 1,000 to 1 and 1 to 1 whether in-solution or in a solid composition.

Buffers are used to adjust the pH so as to optimize enzyme activity. With the phosphate (as the X-oxy group) substituted dioxetanes the pH is between 9 and 10 so that non-enzymatic hydrolysis of the phosphate group is minimized resulting in low background luminescence. 2-Methyl 2-amino-1-propanal (221) is a preferred buffer. Other buffers are tris(hydroxymethyl)aminomethane and carbonate. Inorganic salts such as magnesium acetate are also used to activate the enzyme. The buffer system is chosen to provide maximal catalytic activity for the enzyme and an acceptor for the X-oxy group cleaved from the dioxetane, such as the phosphate.

The present invention incorporates a stable dioxetane and fluorescent energy acceptor, preferably in organized molecular assemblies such as micelles affording efficient energy transfer These procedures are applicable with other types of organized assemblies including reversed micelles, liposomes, microemulsions, films, monolayers and polymers.

It will be appreciated that the dioxetane and acceptor can be in solution in a solvent or in a solid form such as on a film. The solid phase provides ease of positioning these molecules together.

It is intended that the foregoing description be only illustrative and that the present invention be limited only by the hereinafter appended claims.

I claim:
1. A composition which generates light upon triggering which comprises in admixture:
(a) a fluorescent compound; and
(b) a stable 1,2-dioxetane of the formula:

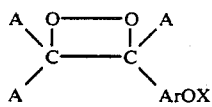

wherein ArOX represents an aryl group substituted with an X-oxy group which forms an unstable oxide intermediate 1,2-dioxetane compound when triggered to remove X by an activating agent so that the unstable 1,2-dioxetane compound decomposes and releases electronic energy to form light and two carbonyl containing compounds of the formula:

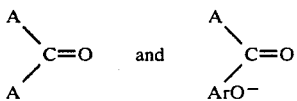

wherein X is a chemically labile group which is removed by the activating agent to form the unstable oxide intermediate 1,2-dioxetane and wherein A are passive organic groups which allow the light to be produced wherein the stable 1,2-dioxetane is decomposed with the activating agent wherein the dioxetane and the fluorescent compound are provided in a closely spaced relationship in the presence of a surfactant, micelle, liposome, reversed micelle, microemulsion, film, including a monolayer, or polymer and wherein the fluorescent compound accepts the electronic energy generated upon decomposition of the unstable oxide intermediate and produces a more intense light than is produced by the triggering of the dioxetane alone.

2. A composition which generates light upon triggering which comprises in admixture:
(a) a fluorescent compound; and
(b) a stable 1,2-dioxetane compound of the formula:

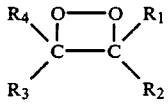

wherein one of $R_1$ and $R_2$ together and $R_3$ and $R_4$ together can be joined as spirofused alkylene which can contain hetero atoms selected from the group consisting of N, S, O and P in addition to carbon and aryl rings, wherein at least one of $R_1$ and $R_2$ or $R_3$ and $R_4$ is an aryl group substituted with an X-oxy group which forms an unstable oxide intermediate 1,2 dioxetane compound when triggered to remove X by an activating agent selected from acids, bases, salts, enzymes, inorganic and organic catalysts and electron donors so that the unstable 1,2-dioxetane compound decomposes and releases electronic energy to form light and two carbonyl containing compounds of the formula:

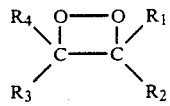

wherein those of $R_1$, $R_2$, $R_3$ or $R_4$ which are unsubstituted by an X-oxy group are organic groups which provide stability for the stable 1,2-dioxetane compound and wherein X is a chemically labile group which is removed by the activating agent to form the unstable oxide intermediate wherein the stable 1,2-dioxetane is decomposed with the activating agent, wherein the dioxetane and the fluorescent compound are provided n a closely spaced relationship in the presence of a surfactant, micelle, liposome, reversed micelle, microemulsion, film, including a monolayer, or polymer and wherein the fluorescent compound accepts the electronic energy generated upon decomposition of the unstable oxide intermediate and produces a more intense light than is produced by the triggering of the dioxetane alone.

3. A composition which generates light upon triggering which comprises in admixture:
(a) a fluorescent compound; and
(b) a stable dioxetane compound of the formula:

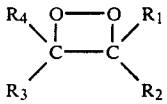

wherein $R_1$ is selected from alkyl, alkoxy, aryloxy dialkylamino, trialkyl or aryl silyloxy and aryl groups including spirofused aryl groups with $R_2$, wherein $R_2$ si an aryl group which can include $R_1$ and is substituted with an X-oxy group which forms an unstable oxide intermediate 1,2-dioxetane compound when triggered to remove X by an activating agent selected from acids, bases, salts, enzymes, inorganic and organic catalysts and electron donors so that the unstable 1,2-dioxetane compound decomposes and releases electronic energy to form light and two carbonyl containing compounds of the formula:

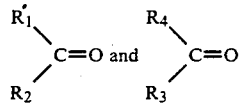

wherein X is a chemically labile group which is removed by the activating agent to form the unstable oxide intermediate and wherein $R_3$ and $R_4$ are selected from aryl, heteroalkyl and alkyl groups which can be joined together as spirofused polycyclic alkyl and polycyclic aryl groups wherein the stable 1,2-dioxetane is decomposed with the activating agent, wherein the dioxetane and the fluorescent compound are provided in a closely spaced relationship in the presence of a surfactant, micelle, liposome, reversed micelle, microemulsion, film, including a monolayer, or polymer and wherein the fluorescent compound accepts the electronic energy generated upon decomposition of the unstable oxide intermediate and produces a more intense light than is produced by the triggering of the dioxetane alone.

4. The composition of claim 1 wherein the mole ratio of dioxetane to fluorescent compound is between about 1,000 to 1 and 1 to 1.

5. The composition of claim 1 wherein the fluorescent compound is a fluorescein compound.

6. The composition of claim 1 wherein in addition a surfactant is provided in the composition.

7. The composition of claim 2 wherein $R_1$ is a methoxy group and $R_2$ is a phenyl group substituted with an X-oxy group and wherein $R_3$ and $R_4$ are joined together as an adamantyl group.

8. The composition of claim 7 wherein the X-oxy group is selected from hydroxyl, trialkyl or aryl silyloxy, inorganic oxyacid salt, oxygen-pyranoside, arylcarboxyl esters and alkylcarboxyl esters and wherein X is removed by the activating agent.

9. The composition of claim 8 wherein the fluorescent compound is a fluorescein compound.

10. The composition of claim 1 wherein a cationic surfactant is provided in the composition, wherein the fluorescent compound is chemically linked with a hydrocarbon chain to provide a fluorescent hydrocarbon which acts as a co-surfactant with a cationic surfactant to increase the light from the dioxetane and fluorescent compound and wherein the dioxetane is present in an amount between about $10^{-2}$ to $10^{-6}$ M, the surfactant is present in an amount greater than $10^{-4}$ M and the co-surfactant is present in an amount between $10^{-3}$ to $10^{-6}$ M.

11. The composition of claim 10 wherein the cationic surfactant is a cetyltrimethylammonium salt.

12. The composition of claim 1 wherein the dioxetane and fluorescent compound are in a closely spaced relationship in a micelle, liposome, reversed micelle, microemulsion, film, monolayer or polymer.

13. The composition of claim 1 wherein the 1,2-dioxetane has the formula:

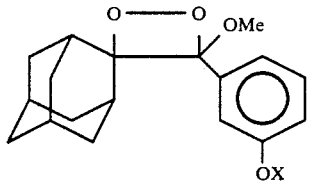

ps wherein X is a group reactive with the activating agent to produce the two carbonyl containing compounds

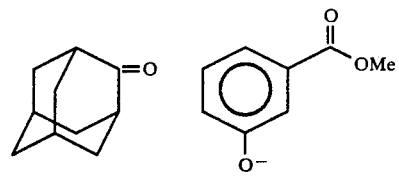

and light.

14. The composition of claim 13 wherein OX is a phosphate group and the activating agent is alkaline phosphatase.

15. The composition of claim 13 wherein in addition a surfactant is admixed in the composition.

16. The composition of claim 15 wherein the surfactant is a cetyltrimethylammonium salt.

17. The composition of claim 13 wherein the fluorescent compound is a fluorescein compound.

18. The composition of claim 17 wherein in addition a surfactant is admixed in the composition.

19. The composition of claim 18 wherein the surfactant is a cetyltrimethylammonium salt.

20. The composition of claim 17 wherein the fluorescein compound is fluorescein chemically linked to a hydrocarbon to provide a fluorescein surfactant.

21. The composition of claim 13 wherein the fluorescent compound is selected from the group consisting of 5-N-tetradecanoylaminofluorescein and 1-hexadecyl-6-hydroxy-2-benzothiazamide.

22. The composition of claim 21 wherein in addition a non-fluorescent surfactant is admixed in the composition.

23. The composition of claim 22 wherein the surfactant is a cetyltrimethylammonium salt.

24. The composition of claim 1 wherein the fluorescent compound is fluorescein chemically linked to a hydrocarbon to provide a fluorescein surfactant which increases the light from the fluorescein compound and the dioxetane.

25. The composition of claim 1 wherein the fluorescent compound is selected from the group consisting of 5-N-tetradecanoylaminofluorescein and 1-hexadecyl-6-hydroxy-2-benzothiazamide.

26. The composition of claim 25 wherein in addition a surfactant is admixed in the composition.

27. The composition of claim 26 wherein the surfactant is a cetyltrimethylammonium salt.

28. The composition of claim 3 wherein the fluorescent compound is fluorescein chemically linked to a hydrocarbon to provide a fluorescein surfactant.

29. The composition of claim 3 wherein the fluorescent compound is selected from the group consisting of 5-N-tetradecanoylaminofluorescein and 1-hexadecyl-6-hydroxy-2-benzothiazamide.

30. The composition of claim 29 wherein in addition a surfactant is admixed in the composition.

31. The composition of claim 30 wherein the surfactant is a cetyltrimethylammonium salt.

32. The composition of claim 1 wherein the dioxetane and the fluorescent compound are provided in a closely spaced relationship in a solid or liquid medium.

33. The composition of claim 2 wherein the dioxetane and the fluorescent compound are provided in a closely spaced relationship in a solid or liquid medium.

34. The composition of claim 3 wherein the dioxetane and the fluorescent compound are provided in a closely spaced relationship in a solid or liquid medium.

35. The composition of claim 3 wherein in addition a surfactant is provided in the composition.

* * * * *

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Page 2, Column 1, line 30, "handley" should be -- Handley --.

Column 2, first structure, the "F" in the last section, both occurrences, should be -- F' --.

Column 2, line 59, after "hyde" and before "However", insert a period --.--.

Column 3, line 47, "Droxetanes" should be --Dioxetanes--.

Column 3, line 49, "hinderad" should be --hindered--.

Column 4, line 17, after "(1974)" insert a period --.--.

Column 4, line 55, after "light" and before "kinetic", insert a period --.--.

Column 4, line 35, after "hours" and before "Neither", insert a period --.--.

Column 5, line 52, after "formate" and before "Addition", insert a period --.--.

Column 6, line 4, after "Dioxetane" and before "Using", insert a period --.--

Column 6, line 10, "tydrophobic", should be --hydrophobic--.

Column 6, line 11, after "factors" and before "Aqueous", insert a period --.--.

UNITED STATES PATENT AND TRADEMARK OFFICE
CERTIFICATE OF CORRECTION

Page 2 of 8

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 6, line 20, after "co-surfactant" and before "No", insert a period --.--.

Column 6, line 21, after "micelles" and before Goto", insert a period --.--.

Column 6, line 56, after "enzyme" and before "Cationic", insert a period --.--

Column 7, line 8, "Soc., 6", should be --Soc., 96--.

Column 7, line 16 "No. 87" should be --No. 887--.

Column 7, line 64, "Bruce", should be --Bunce--.

Column 8, line 11, after "1,2-dioxetanes" and before "Further", insert a period --.--.

Column 9, line 3, after "film" and before "Solutions", insert a period --.--.

Column 9, line 7, after "minutes" and before "Quantities", insert a period --.--.

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 9, line 30, "chemiluminscent" should be --chemiluminescent--.

Column 12, line 5, after "pound" and before "Possible", insert a period --.--.

Column 12, lines 19, 40 and 55, the structures should read as follows:

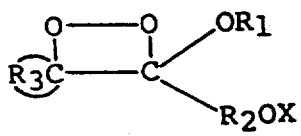 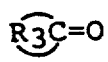 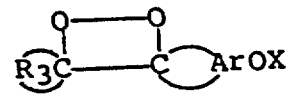

Column 13, line 4, after "atoms" and before "In", insert a period --.--.

Column 14, line 67, after "stability" and before "For", insert a period --.--.

Column 14, line 37, "teen" should be --been--.

Column 14, line 41, "intermolecrlar" should be --intermolecular--.

UNITED STATES PATENT AND TRADEMARK OFFICE
CERTIFICATE OF CORRECTION

PATENT NO. : 5,004,565

DATED : April 2, 1991

INVENTOR(S) : Arthur P. Schaap

It is certified that error appears in the above-indentified patent and that said Letters Patent is hereby corrected as shown below:

Column 15, line 39, after "produced" and before "Chemiluminescence", insert a period --.--.

Column 16, line 62, after "2-adamantanone" and before "The", insert a period --.--.

Column 17, line 53, after "process" and before "The", insert a period --.--.

Column 17, line 61, after "Solution" and before "A", insert a period --.--.

Column 19, line 25, "1,4-dioxade" should be --1,4-dioxane--.

Column 19, line 30, SiLica" should be --Silica--.

Column 20, line 17 "3-cetoxyphenyl" should be --3-Acetoxyphenyl--.

Column 20, line 30, "045 g" should be --0.45 g--.

Column 21, line 42, after "material" and before "Column", insert a period --.--.

Column 22, line 34, "157 63" should be --157.63--.

Column 22, line 35, "160.4(," should be --160.48,--.

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 23, line 5, "w[en" should be --when--.

Column 23, line 8, "1H NMR" should be --$^1$H NMR--.

Column 23, line 11, "1H NMR" should be --$^1$H NMR--.

Column 23, line 13, "D20), 6.93 7.30" should read -- $D_{20}$), 6.93-7.30 --.

Column 23, line 13, "13C NMR" should be -- $^{13}$C NMR --.

Column 23, line 18, "3,2'-adamantanel (2b)" should be -- 3,2'-adamantane] (2b) --.

Column 23, line 23, after "2.5 h." and before "NMR", the following should be inserted --Filtration and removal of solvent produced 2b as an oil: $^1$H --.

Column 25, line 39 "($\Phi_{cl}$)" should be -- ($\Phi_{CL}$) --.

Column 26, line 6, in the structure "$\Phi_{cl}$" should be -- ($\Phi_{CL}$ --.

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 26, line 36, after "water" and before "However", insert a period --.--.

Column 26, line 43, "$\Phi_{Cl}$", should be -- $\Phi_{CL}$ --.

Column 26, line 68, "03%" should be -- 0.3% --.

Column 27, line 1, "Dioxet" should be --Dioxetane--.

Column 27, line 22, after "(FIG 4)" and before "The", insert a period --.--.

Column 27, line 58, "$\Phi_{Cl}$" should be -- $\Phi_{CL}$ --.

Column 27, line 64, "il" should be --in--.

Column 28, line 8, after "period" and before "Integration", insert a period --.--.

Column 28, line 10, "$\Phi_{Cl}$", should be -- $\Phi_{CL}$ --.

Column 28, line 14, "stifted", should be -- shifted --.

Column 28, line 19, "cf" should be -- of --.

Column 28, line 31, after "phosphatase" and before "A", insert a period --.--.

Column 28, line 34, "cf", should be --of --.

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 28, line 58, after "correlations" and before "For", insert a period --.--.

Column 29, line 10, "2.3 x 10-17" should be --2.3 x $10^{-17}$ --.

Column 29, line 12, after "10%" and before "Under", insert a period --.--.

Column 29, line 61, "1 36" should be -- 1.36 --.

Column 29, line 64, "The" should be --the--.

Column 30, line 12, after "temperature" and before "It", insert a period --.--.

Column 30, line 35, "10-4" should be -- $10^{-4}$ --.

Column 30, line 58, after "transfer" and before "These", insert a period --.--.

Column 30, line 47, "propanal" should be --propanol--.

Column 32, lines 1-7, the structure should read as follows:

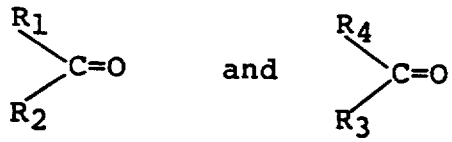

UNITED STATES PATENT AND TRADEMARK OFFICE
CERTIFICATE OF CORRECTION

PATENT NO. : 5,004,565
DATED : April 2, 1991
INVENTOR(S) : Arthur P. Schaap

It is certified that error appears in the above-indentified patent and that said Letters Patent is hereby corrected as shown below:

Column 32, line 16, "provided n" should read -- provided in --.

Column 32, line 38, "si" should be -- is --.

Column 33, line 49, before "wherein", the "ps" should be deleted.

Signed and Sealed this

Seventeenth Day of January, 1995

Attest:

BRUCE LEHMAN

Attesting Officer

Commissioner of Patents and Trademarks